US012611091B2

(12) United States Patent
Nakai et al.

(10) Patent No.: US 12,611,091 B2
(45) Date of Patent: Apr. 28, 2026

(54) FLEXIBLE TUBE FOR ENDOSCOPE, ENDOSCOPIC MEDICAL DEVICE, AND METHODS FOR PRODUCING THE SAME

(71) Applicant: FUJIFILM Corporation, Tokyo (JP)

(72) Inventors: Yoshihiro Nakai, Kanagawa (JP); Kazuma Horita, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 331 days.

(21) Appl. No.: 18/325,122

(22) Filed: May 30, 2023

(65) Prior Publication Data

US 2023/0292998 A1 Sep. 21, 2023

Related U.S. Application Data

(63) Continuation of application No. PCT/JP2021/043514, filed on Nov. 29, 2021.

(30) Foreign Application Priority Data

Dec. 24, 2020 (JP) ................................. 2020-215764

(51) Int. Cl.
*A61B 1/005* (2006.01)
*A61B 1/00* (2006.01)

(52) U.S. Cl.
CPC .......... *A61B 1/0055* (2013.01); *A61B 1/0011* (2013.01)

(58) Field of Classification Search
CPC ............................ A61B 1/0055; A61B 1/0011
See application file for complete search history.

(56) References Cited

U.S. PATENT DOCUMENTS 2,626,223 A * 1/1953 Sattler ..................... C08L 77/12
525/428
2010/0036201 A1 2/2010 Ogura
(Continued)

FOREIGN PATENT DOCUMENTS

EP 3653104 5/2020
JP S59137030 8/1984
(Continued)

OTHER PUBLICATIONS

"Search Report of Europe Counterpart Application", issued on Jan. 24, 2024, pp. 1-5.
(Continued)

*Primary Examiner* — Michael J Carey
*Assistant Examiner* — Megan Elizabeth Monahan
(74) *Attorney, Agent, or Firm* — JCIPRNET

(57) ABSTRACT

Provided are a flexible tube for an endoscope, the flexible tube having good elasticity, being capable of sufficiently maintaining adhesiveness between a flexible-tube base and a polymer cover layer covering the flexible-tube base even when repeatedly exposed to heat for a long time, and being less likely to undergo a decrease in the adhesiveness between the flexible-tube base and the polymer cover layer even when subjected to disinfection treatment with a hydrogen peroxide solution, an endoscopic medical device including the flexible tube for an endoscope, and methods for producing the flexible tube and the endoscopic medical device.

The flexible tube for an endoscope has a flexible-tube base containing metal as a constituent material, a layer containing a siloxane compound and disposed on the flexible-tube base, a primer layer on the layer containing the siloxane compound, and a polymer cover layer on the primer layer. The siloxane compound has a hydroxy group. The polymer cover (Continued)

layer includes at least one compound of a polyamide, a polyester, a polyurethane, or a polyolefin on a side in contact with the primer layer.

14 Claims, 4 Drawing Sheets

(56) References Cited

U.S. PATENT DOCUMENTS

| | | | |
|---|---|---|---|
| 2011/0245612 A1 | 10/2011 | Nakamura | |
| 2020/0100652 A1* | 4/2020 | Yoshitani | C08K 5/5415 |
| 2021/0380853 A1 | 12/2021 | Nakai et al. | |

FOREIGN PATENT DOCUMENTS

| | | |
|---|---|---|
| JP | H08234115 | 9/1996 |
| JP | H1142205 | 2/1999 |
| JP | 2002065590 | 3/2002 |
| JP | 2010035923 | 2/2010 |
| JP | 2011212338 | 10/2011 |
| WO | WO-2019013243 A1 * | 1/2019 ........... C09J 175/06 |
| WO | 2020175277 | 9/2020 |

OTHER PUBLICATIONS

"International Search Report (Form PCT/ISA/210) of PCT/JP2021/043514", mailed on Feb. 1, 2022, with English translation thereof, pp. 1-5.

"Written Opinion of the International Searching Authority (Form PCT/ISA/237) of PCT/JP2021/043514", mailed on Feb. 1, 2022, with English translation thereof, pp. 1-6.

* cited by examiner

FIG. 3

FLEXIBLE TUBE FOR ENDOSCOPE, ENDOSCOPIC MEDICAL DEVICE, AND METHODS FOR PRODUCING THE SAME

CROSS-REFERENCE TO RELATED APPLICATIONS

This application is a Continuation of PCT International Application No. PCT/JP2021/043514 filed on Nov. 29, 2021, which claims priority under 35 U.S.C. § 119 (a) to Japanese Patent Application No. 2020-215764 filed in Japan on Dec. 24, 2020. Each of the above applications is hereby expressly incorporated by reference, in its entirety, into the present application.

BACKGROUND OF THE INVENTION

1. Field of the Invention

The present invention relates to a flexible tube for an endoscope, an endoscopic medical device, and methods for producing the same.

2. Description of the Related Art

Endoscopes are medical devices for examining the inside of the body cavity, the inside of the digestive tract, the esophagus, or the like of a patient. Since endoscopes are inserted and used in the body, it is desirable to provide endoscopes that do not damage organs or cause pain or discomfort to a patient. In view of such a requirement, a spiral tube formed by spirally winding a soft, bendable metal strip is used for a flexible tube constituting an insertion section (structural section to be inserted into the body cavity) of an endoscope. Furthermore, the periphery of the spiral tube is covered with a flexible polymer, and this polymer cover layer is covered with a topcoat layer as required so as not to cause stimulation or damage to the inner surface of, for example, the esophagus, digestive tract, or body cavity.

The flexible tube is required to have high elasticity in order to move smoothly in the body. By increasing elasticity of the flexible tube, the flexible tube that has passed through a bent portion in the body easily returns to a straight shape, and the burden on the subject during a test can be further reduced. For example, JP2010-035923A discloses, as a technology that meets this requirement, that, after a primer is applied to a surface of a metal core member (flexible-tube base), an outer cover layer is formed to cover the primer, and that a silane coupling agent, a titanate-based coupling agent, an aluminum-based coupling agent, and a zirconium-based coupling agent can be used as the primer. According to JP2010-035923A, this flexible tube for an endoscope has good elasticity.

SUMMARY OF THE INVENTION

Meanwhile, to improve, for example, operability and durability of an endoscope, it is important to enhance adhesiveness between a flexible-tube base and a polymer cover layer that covers the flexible-tube base. If this adhesiveness is insufficient, when a flexible tube is inserted into the body, for example, a crease, lifting, tearing, or separation tends to occur in the polymer cover layer by bending the flexible tube, and when the flexible tube is rotated in the inserted state, twisting of the polymer cover layer tends to occur. If such a crease, lifting, tearing, separation, or twisting occurs in the polymer cover layer, for example, the surface of the flexible tube inserted in the body may catch the surrounding tissues, which may cause a pain to the subject.

The endoscope is repeatedly exposed to heat generated from, for example, an illumination light source housed within the endoscope each time the endoscope is used. Further, each time the endoscope is used, the endoscope is subjected to disinfection treatment or sterilization treatment with a chemical solution and thus is also repeatedly exposed to heat at about 60° C. As a result of studies conducted by the inventors of the present invention, it has been found that when the flexible tube for an endoscope disclosed in JP2010-035923A is repeatedly exposed to heat, the above adhesiveness tends to decrease. Accordingly, the flexible tube for an endoscope is required to have good thermal durability for a long time (i.e., a property that the adhesiveness is less likely to decrease even when repeatedly exposed to heat).

It has also been found that the adhesiveness of the flexible tube for an endoscope described in JP2010-035923A tends to decrease when the flexible tube is repeatedly subjected to disinfection treatment with a hydrogen peroxide solution having a strong oxidizing power. This is probably because a primer component is oxidatively decomposed by hydrogen peroxide, and in particular, hydrogen peroxide is activated by the surface of the metal base.

In view of the above, an object of the present invention is to provide a flexible tube for an endoscope, the flexible tube having good elasticity, being capable of sufficiently maintaining adhesiveness between a flexible-tube base and a polymer cover layer covering the flexible-tube base even when repeatedly exposed to heat for a long time, and being less likely to undergo a decrease in the adhesiveness between the flexible-tube base and the polymer cover layer even when repeatedly subjected to disinfection treatment with a hydrogen peroxide solution, and an endoscopic medical device including the flexible tube for an endoscope. Another object of the present invention is to provide a method for producing the flexible tube for an endoscope and a method for producing the endoscopic medical device.

In view of the above problems, the inventors of the present invention have conducted extensive studies on formation of a polymer cover layer in a flexible tube for an endoscope. As a result, the inventors have found that the objects can be achieved by forming a layer using a siloxane compound having a hydroxy group on a surface of a flexible-tube base made of a metal material, forming a primer layer on the layer containing the siloxane compound, and further using a specific polymer as a constituent material of a polymer cover layer that is in contact with the primer layer. Further studies have been conducted on the basis of these findings, and the present invention has been completed.

The above objects of the present invention have been achieved by the following means.

<1>

A flexible tube for an endoscope, the flexible tube having a flexible-tube base containing metal as a constituent material; a layer containing a siloxane compound and disposed on the flexible-tube base; a primer layer on the layer containing the siloxane compound; and a polymer cover layer on the primer layer, wherein the siloxane compound has a hydroxy group, and the polymer cover layer includes at least one compound of a polyamide, a polyester, a polyurethane, or a polyolefin on a side in contact with the primer layer.

<2>

The flexible tube for an endoscope according to <1>, wherein the siloxane compound includes an organosiloxane compound.

<3>

The flexible tube for an endoscope according to <1> or <2>, wherein the primer layer includes at least one of a silane coupling agent, a titanium coupling agent, a zirconium coupling agent, or an aluminum coupling agent.

<4>

The flexible tube for an endoscope according to any one of <1> to <3>, wherein the primer layer includes a silane coupling agent.

<5>

The flexible tube for an endoscope according to any one of <1> to <4>, wherein the primer layer includes an amino silane coupling agent.

<6>

The flexible tube for an endoscope according to any one of <1> to <5>, wherein the metal that constitutes the flexible-tube base is stainless steel.

<7>

The flexible tube for an endoscope according to any one of <1> to <6>, wherein the metal that constitutes the flexible-tube base has a passivation film on a surface of the metal.

<8>

The flexible tube for an endoscope according to any one of <1> to <7>, wherein the polymer cover layer has a single-layer structure or a multilayer structure and includes at least one compound of a polyamide, a polyester, a polyurethane, or a polyolefin in a layer in contact with the primer layer.

<9>

The flexible tube for an endoscope according to any one of <1> to <8>, wherein the polymer cover layer has a two-layer structure, and a proportion of a thickness of an inner layer to a thickness of an outer layer of the two-layer structure changes in a gradient manner in an axial direction of the flexible-tube base.

<10>

The flexible tube for an endoscope according to any one of <1> to <9>, wherein the proportion of the thickness of the inner layer to the thickness of the outer layer is inner layer:outer layer=95:5 to 60:40 at one end of the flexible tube for an endoscope and is inner layer:outer layer=5:95 to 40:60 at the other end.

<11>

An endoscopic medical device having the flexible tube for an endoscope according to any one of <1> to <10>.

<12>

A method for producing a flexible tube for an endoscope, the method including forming, on a flexible-tube base containing metal as a constituent material, a layer containing a siloxane compound; forming a primer layer on the layer containing the siloxane compound; and forming a polymer cover layer on the primer layer, wherein the siloxane compound has a hydroxy group, and the polymer cover layer includes at least one compound of a polyamide, a polyester, a polyurethane, or a polyolefin on a side in contact with the primer layer.

<13>

A method for producing an endoscopic medical device, the method including incorporating, into an insertion section of an endoscopic medical device, a flexible tube for an endoscope obtained by the method for producing a flexible tube for an endoscope according to <12>.

<14>

A method for producing an endoscopic medical device, the method including incorporating, into an insertion section of an endoscopic medical device, the flexible tube for an endoscope according to any one of <1> to <10>.

In the present specification, when a plurality of substituents, linking groups, or the like (hereinafter referred to as substituents or the like) represented by specific symbols are present or a plurality of substituents or the like are defined simultaneously or alternatively, the substituents or the like may be the same or different from each other. In addition, even if not specifically stated, when a plurality of substituents or the like are adjacent to each other, they may be linked or fused to each other to form a ring.

In the present specification, a substituent for which substitution or non-substitution is not specified (the same applies to a linking group) means that the group may have any substituent as long as the desired effect is achieved. The same applies to a compound for which substitution or non-substitution is not specified.

In the present specification, when the number of carbon atoms of a group is specified, the number of carbon atoms means the number of carbon atoms of the whole group. That is, when this group is in a form further having a substituent, the number of carbon atoms means the number of carbon atoms of the whole that includes this substituent.

The flexible tube for an endoscope according to the present invention has good elasticity, can sufficiently maintain adhesiveness between a flexible-tube base and a polymer cover layer covering the flexible-tube base even when repeatedly exposed to heat for a long time, and is less likely to undergo a decrease in the adhesiveness between the flexible-tube base and the polymer cover layer even when repeatedly subjected to disinfection treatment with a hydrogen peroxide solution.

In the endoscopic medical device according to the present invention, a flexible tube, which is a structural section to be inserted into the body, has good elasticity, can sufficiently maintain adhesiveness between a flexible-tube base and a polymer cover layer covering the flexible-tube base even when repeatedly exposed to heat for a long time, and is less likely to undergo a decrease in the adhesiveness between the flexible-tube base and the polymer cover layer even when repeatedly subjected to disinfection treatment with a hydrogen peroxide solution. Accordingly, the endoscopic medical device according to the present invention has good durability and can further reduce the burden on the subject during use.

The method for producing a flexible tube for an endoscope according to the present invention can provide a flexible tube for an endoscope, the flexible tube having good elasticity, being capable of sufficiently maintaining adhesiveness between a flexible-tube base and a polymer cover layer covering the flexible-tube base even when repeatedly exposed to heat for a long time, and being less likely to undergo a decrease in the adhesiveness between the flexible-tube base and the polymer cover layer even when repeatedly subjected to disinfection treatment with a hydrogen peroxide solution.

According to the method for producing an endoscopic medical device according to the present invention, a flexible tube constituting the device can have good elasticity and have properties of sufficiently maintaining adhesiveness between a flexible-tube base and a polymer cover layer covering the flexible-tube base even when repeatedly exposed to heat for a long time and being less likely to undergo a decrease in the adhesiveness between the flexible-tube base and the polymer cover layer even when repeatedly subjected to disinfection treatment with a hydrogen peroxide solution. Accordingly, the method for producing an endoscopic medical device according to the present invention can provide an endoscopic medical device that has good durability and that further reduces the burden on the subject during use.

BRIEF DESCRIPTION OF THE DRAWINGS

FIG. 3 is a block diagram illustrating the configuration of an apparatus for producing a flexible tube for an endoscope according to an embodiment.

DESCRIPTION OF THE PREFERRED EMBODIMENTS

Figure 1:
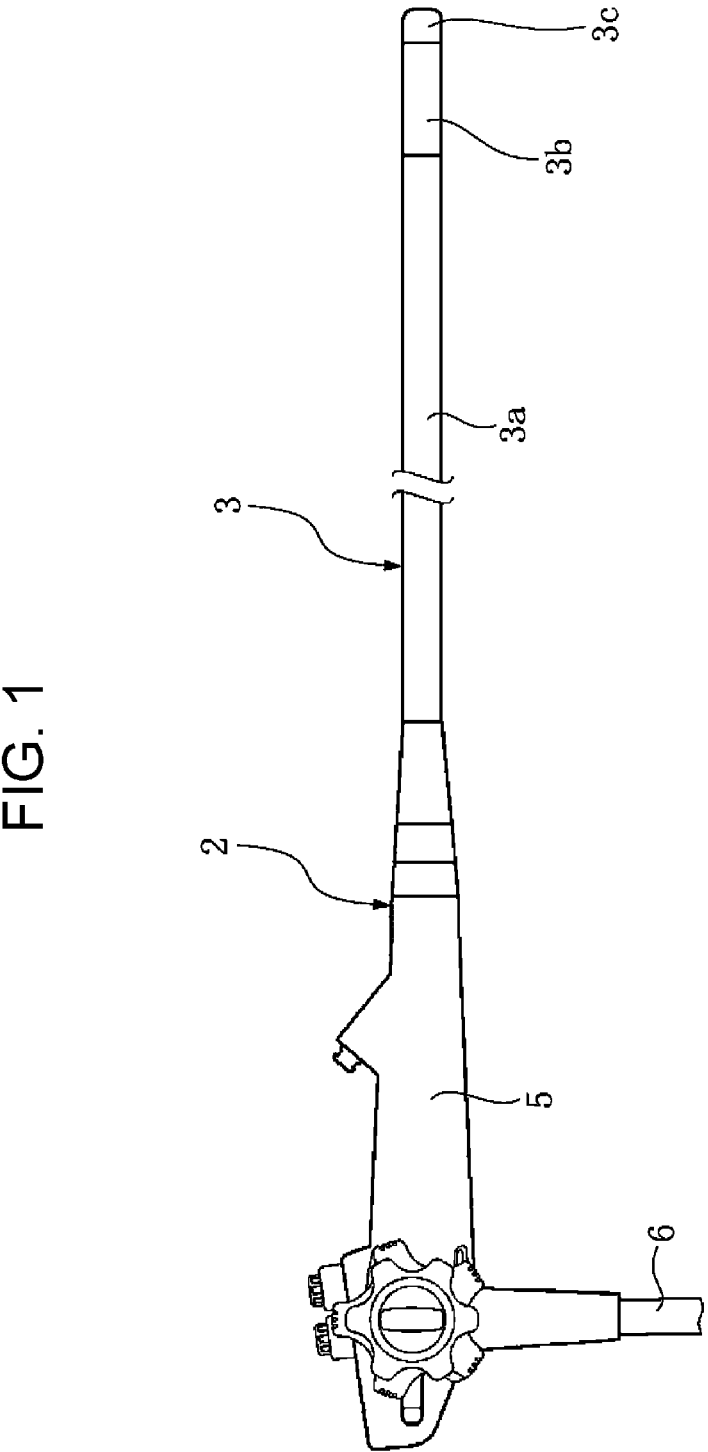
FIG. 1 is an external view illustrating the configuration of an electronic endoscope according to an embodiment.

A preferred embodiment of an endoscopic medical device in which a flexible tube for an endoscope (hereinafter, the flexible tube for an endoscope may be simply referred to as a "flexible tube") according to the present invention is incorporated will be described by taking an electronic endoscope as an example. The electronic endoscope is used as a medical device for, for example, observing the inside of the body by inserting the flexible tube into the body cavity, the digestive tract, the esophagus, or the like. In an example illustrated in FIG. 1, an electronic endoscope 2 includes an insertion section 3 to be inserted into the body, a main-body operation section 5 connected to a proximal end portion of the insertion section 3, and a universal cord 6 to be connected to a processor device or a light source device. The insertion section 3 is constituted by a flexible tube 3a connected to the main-body operation section 5, an angle portion 3b connected to the flexible tube 3a, and a tip portion 3c connected to the distal end of the angle portion 3b and including therein an imaging device (not illustrated) for capturing an image of the inside of the body. The flexible tube 3a, which accounts for most of the length of the insertion section 3, has flexibility across substantially the entire length thereof and is configured so that, in particular, a portion to be inserted into the inside of the body cavity or the like has higher flexibility. In FIG. 1, the angle portion 3b side has a soft structure (soft), and the main-body operation section 5 side has a hard structure (hard).

Flexible Tube for Endoscope

A flexible tube for an endoscope according to the present invention has a flexible-tube base containing metal as a constituent material, a layer containing a siloxane compound and disposed on the flexible-tube base, a primer layer on the layer containing the siloxane compound, and a polymer cover layer on the primer layer.

The siloxane compound has at least one of a hydrolyzable group or a hydroxy group.

The polymer cover layer includes at least one compound of a polyamide, a polyester, a polyurethane, or a polyolefin on a side in contact with the primer layer. That is, the flexible tube for an endoscope has a flexible-tube base containing metal as a constituent material, a layer containing a siloxane compound (hereinafter, also referred to as a "siloxane compound-containing layer"), a primer layer, and a polymer cover layer in this order, in which the siloxane compound has a hydroxy group, and the polymer cover layer includes at least one compound of a polyamide, a polyester, a polyurethane, or a polyolefin on a side in contact with the primer layer.

Figure 2:
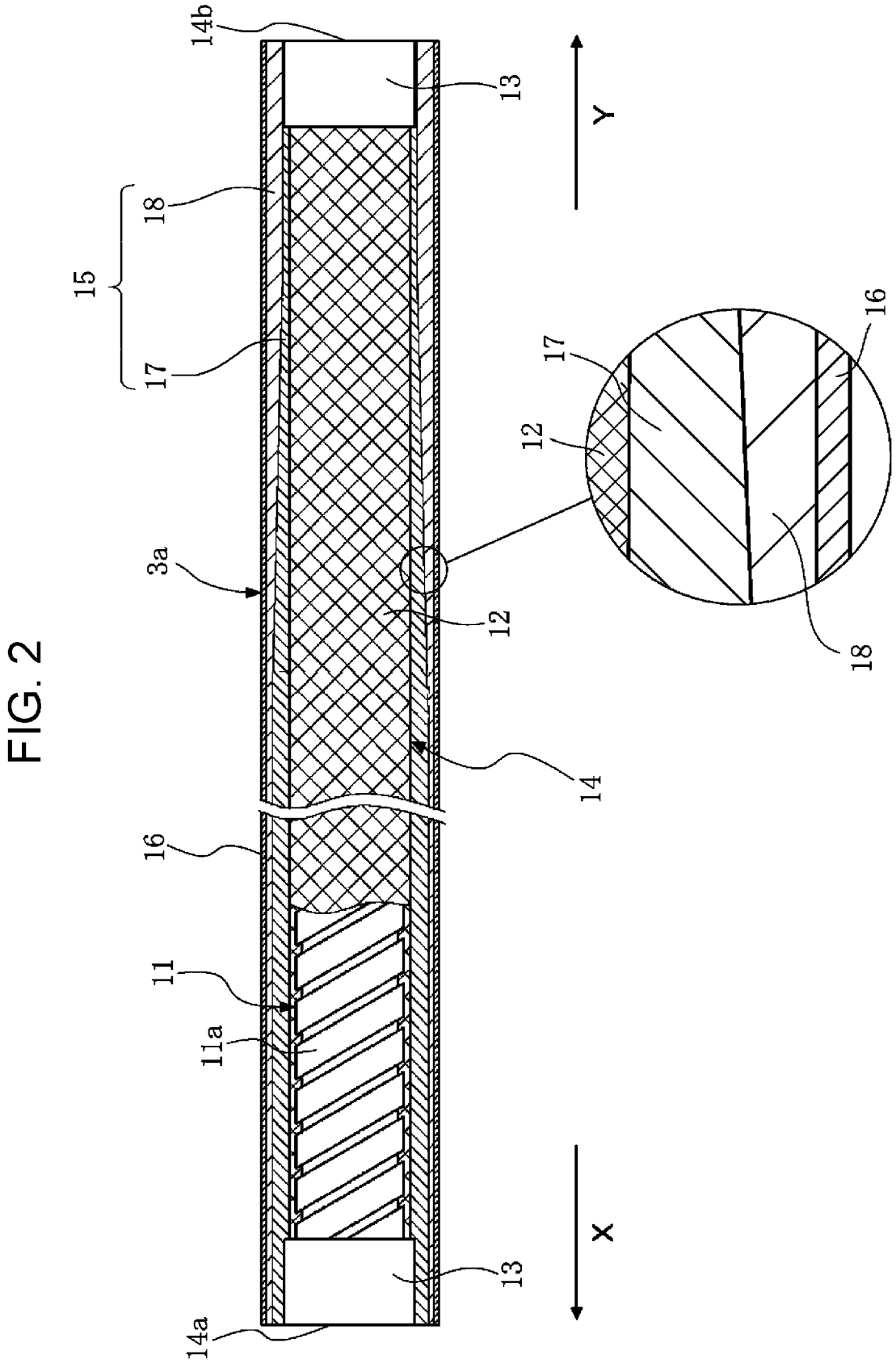
FIG. 2 is a partial sectional view illustrating the configuration of a flexible tube for an endoscope according to an embodiment.

In FIG. 2, the siloxane compound-containing layer and the primer layer are not illustrated.

The flexible tube for an endoscope according to the present invention has good elasticity, can sufficiently maintain adhesiveness between a flexible-tube base and a polymer cover layer covering the flexible-tube base even when repeatedly exposed to heat for a long time, and is less likely to undergo a decrease in the adhesiveness between the flexible-tube base and the polymer cover layer even when repeatedly subjected to disinfection treatment with a hydrogen peroxide solution. Although the reason for this is not clear, this is probably because, for example, the siloxane compound-containing layer itself exhibits high resistance to hydrogen peroxide, and the number of covalent bonds (for example, ether bonds) between the primer layer and the flexible-tube base layer increases.

Flexible-Tube Base

The flexible tube has, as an innermost layer, a flexible-tube base containing metal as a constituent material.

As illustrated in FIG. 2, a flexible-tube base 14 preferably has a form in which a spiral tube 11 disposed on the innermost side and formed by spirally winding a metal strip 11a is covered with a tubular mesh member 12 formed by weaving metal wires, and caps 13 are fitted to both ends of the flexible-tube base 14. The metal that constitutes the flexible-tube base 14 preferably has a surface that has been subjected to passivation treatment in order to prevent corrosion. That is, the flexible-tube base 14 preferably has a passivation film (for example, a metal oxide film) on the outer periphery thereof. This passivation treatment can be performed by an ordinary method. A passivation film can be formed on a surface of metal by, for example, immersing the metal in a solution including a strong oxidizing agent such as nitric acid, heating the metal in air (oxygen) or water (water vapor), or anodizing the metal in a solution including an oxidizing agent.

The metal that constitutes the flexible-tube base 14 is preferably stainless steel. The surface of stainless steel is usually in a state in which chromium and oxygen are bound together to form a passivation film. However, even when stainless steel is used as the constituent material of the flexible-tube base 14, the stainless steel is preferably subjected to the passivation treatment described above in order to more reliably form a more uniform passivation film over the entire surface of the stainless steel.

Siloxane Compound-Containing Layer

The siloxane compound included in the siloxane compound-containing layer is a compound having a siloxane bond (a repeating structure of [—Si—O]) and is, for example, an oligomer or a polymer obtained by hydrolysis and polycondensation of silane compounds having hydrolyzable groups. Therefore, the siloxane compound has a hydroxy group. The silane compounds may be either inorganic silane compounds or organic silane compounds, and are preferably organic silane compounds. That is, the siloxane compound is preferably an organosiloxane compound.

Examples of the hydrolyzable group include an alkoxy group (an alkyloxy group), an alkenyloxy group, an acyloxy group, an aminooxy group, an oxime group, and an amide group. An alkoxy group is preferred.

The alkyl group in the alkoxy group may be linear, branched, or cyclic. The number of carbon atoms of the alkyl group is preferably 1 to 30, more preferably 1 to 20, still more preferably 1 to 10, and even more preferably 1 or 2. Specific examples of the alkyl group include methyl, ethyl, isopropyl, butyl, and cyclopentyl.

The alkenyl group in the alkenyloxy group may be linear, branched, or cyclic. The number of carbon atoms of the alkenyl group is preferably 2 to 30, more preferably 2 to 20, and still more preferably 2 to 10.

Examples of the organic silane compounds include tetraalkoxysilane compounds, trialkoxysilane compounds, and dialkoxysilane compounds.

Examples of the tetraalkoxysilane include, but are not particularly limited to, tetramethoxysilane, tetraethoxysilane, tetrapropoxysilane, tetraisopropoxysilane, and tetrabutoxysilane.

Examples of the trialkoxysilane compounds include, but are not particularly limited to, methyltrimethoxysilane, methyltriethoxysilane, phenyltrimethoxysilane, and phenyltriethoxysilane.

Examples of the dialkoxysilane compounds include, but are not particularly limited to, dimethyldimethoxysilane and dimethyldiethoxysilane.

The siloxane compound preferably has no organic group other than methyl and ethyl.

The weight-average molecular weight of the siloxane compound is not particularly limited, and is, for example, preferably 100 to 2,000, and more preferably 150 to 500.

The weight-average molecular weight or number-average molecular weight of a compound described in the specification of this application is determined as follows.

The weight-average molecular weight or the number-average molecular weight can be measured by gel permeation chromatography (GPC) as a molecular weight in terms of polystyrene.

Specifically, the measurement can be performed by using a GPC apparatus HLC-8220 (trade name, manufactured by Tosoh Corporation), using tetrahydrofuran as an eluant, using G3000HXL+G2000HXL (both of which are trade names, manufactured by Tosoh Corporation) as columns at 23° C. and at a flow rate of 1 mL/min, and detecting by RI.

Examples of the siloxane compound that can be used in the present invention include compounds used in Examples described later; however, the present invention is not limited to these.

The flexible tube according to the present invention is meant to include a form in which the siloxane compound-containing layer has reacted with at least one of the flexible-tube base or the primer layer. For example, the siloxane compound-containing layer can be present in a state where hydroxy groups of the siloxane compound have reacted with the primer layer or metal constituting the flexible-tube base or have reacted with groups on the surface of the polymer cover layer.

The content of the siloxane compound in the siloxane compound-containing layer is preferably 50% by mass or more, more preferably 70% by mass or more, still more preferably 80% by mass or more, and even more preferably 90% by mass or more. The siloxane compound-containing layer may be a layer composed of a siloxane compound.

In the siloxane compound included in the siloxane compound-containing layer, the organosiloxane content is not particularly limited, and can be, for example, 80% by mass or more, is preferably 90% by mass or more, and may be 100% by mass.

The siloxane compound-containing layer may include components other than the siloxane compound as long as the effects of the present invention are not impaired. Examples of such components include metal alkoxides other than coupling agents described later, binder resins, and stabilizers (such as surfactants and antioxidants).

The average layer thickness of the siloxane compound-containing layer is not particularly limited, but is preferably 5 to 400 nm, more preferably 15 to 300 nm, still more preferably 25 to 150 nm, and even more preferably 40 to 100 nm in view of the elasticity, thermal durability, and hydrogen peroxide solution resistance of the flexible tube.

Primer Layer

The primer layer that constitutes the flexible tube according to the present invention preferably includes at least one of a silane coupling agent, a titanium coupling agent, a zirconium coupling agent, or an aluminum coupling agent in view of elasticity, thermal durability, and hydrogen peroxide solution resistance of the flexible tube.

Preferably, the silane coupling agent does not have a siloxane bond but has an organic group other than methyl, ethyl, methoxy, and ethoxy (for example, a vinyl group, a propyl group, an acid anhydride group, or an epoxy group).

As the silane coupling agent, the titanium coupling agent, the zirconium coupling agent, and the aluminum coupling agent used in the present invention, typical silane coupling agents titanium coupling agents, zirconium coupling agents and aluminum coupling agents applicable to a primer layer of a flexible tube for an endoscope can be widely used. In the present invention, the primer layer preferably includes a silane coupling agent and more preferably includes an amino silane coupling agent (preferably a silane coupling agent having at least one of an unsubstituted amino group or a monosubstituted amino group) in view of elasticity, thermal durability, and hydrogen peroxide solution resistance of the flexible tube. Specific examples of the silane coupling agent, the titanium coupling agent, the zirconium coupling agent, and the aluminum coupling agent include silane coupling agents, titanium coupling agents, zirconium coupling agents, and aluminum coupling agents used in Examples described later, but the present invention is not limited to these.

The content of the silane coupling agent, the titanium coupling agent, the zirconium coupling agent, and the aluminum coupling agent in the primer layer is preferably 50% by mass or more, more preferably 70% by mass or more, still more preferably 80% by mass or more, and even more preferably 90% by mass or more, in total. The primer layer may be a layer composed of at least one of a silane coupling agent, a titanium coupling agent, a zirconium coupling agent, or an aluminum coupling agent.

The molecular weight of each of the silane coupling agent, the titanium coupling agent, the zirconium coupling agent, and the aluminum coupling agent used in the present invention is not particularly limited and is, for example, preferably 100 to 2,000, and more preferably 200 to 500.

A polymer silane coupling agent may also be used.

When the primer layer includes an amino silane coupling agent, the content of the amino silane coupling agent in the silane coupling agent constituting the primer layer is preferably 50% by mass or more, more preferably 70% by mass or more, still more preferably 80% by mass or more, and even more preferably 90% by mass or more.

The primer layer may include components other than the silane coupling agent, the titanium coupling agent, the zirconium coupling agent, and the aluminum coupling agent as long as the effects of the present invention are not impaired. Examples of such components include metal alkoxides other than the above coupling agents, binder resins, and stabilizers such as surfactants and antioxidants.

In the present invention, "the primer layer includes at least one of a silane coupling agent, a titanium coupling agent, a zirconium coupling agent, or an aluminum coupling agent" is meant to include a form in which at least one of a silane coupling agent, a titanium coupling agent, a zirconium coupling agent, or an aluminum coupling agent is included in a state of having reacted with the siloxane compound-containing layer or the flexible-tube base, and a form in which at least one of a silane coupling agent, a titanium coupling agent, a zirconium coupling agent, or an aluminum coupling agent is included in a state of having reacted with the polymer cover layer. That is, a silane coupling agent, a titanium coupling agent, a zirconium coupling agent, and an aluminum coupling agent are at least partially hydrolyzed to expose hydroxy groups, and the coupling agents can be present in a state where the hydroxy groups have reacted with the siloxane compound-containing layer or metal constituting the flexible-tube base or have reacted with groups on the surface of the polymer cover layer.

The layer thickness of the primer layer is significantly smaller than that of a typical adhesive layer (in other words, the concept of the thickness cannot be conceived). That is, the primer layer differs from the adhesive layer that requires a certain layer thickness and softness for adhesion between the flexible-tube base and the polymer cover layer.

Polymer Cover Layer

The flexible tube according to the present invention has a polymer cover layer on the outer periphery of the flexible-tube base on which the siloxane compound-containing layer and the primer layer are disposed in this order.

In the embodiment in FIG. 2, an outer surface of a polymer cover layer 15 is coated with a topcoat layer 16 that contains fluorine or the like and that contributes to, for example, chemical resistance. In FIG. 2, only a single layer of the spiral tube 11 is illustrated, but the spiral tube 11 may be formed by concentrically stacking two or more layers. Note that the polymer cover layer 15 and the topcoat layer 16 in the drawing are drawn to be thicker than the actual thicknesses with respect to the diameter of the flexible-tube base 14 for the sake of clearly illustrating the layer structure.

In the present invention, the polymer cover layer covers the outer peripheral surface of the flexible-tube base having the siloxane compound-containing layer and the primer layer described above. The polymer cover layer 15 in the embodiment in FIG. 2 has a two-layer structure in which an inner layer 17 that covers the entire peripheral surface around the axis of the flexible-tube base 14 and an outer layer 18 that covers the entire peripheral surface around the axis of the inner layer 17 are laminated. Typically, a soft polymer is used as the material of the inner layer 17 and a hard polymer is used as the material of the outer layer 18, but the present invention is not limited to these embodiments.

In the present invention, as described later, when the polymer cover layer has a multilayer structure of two or more layers, at least the innermost layer (layer in contact with the primer layer) includes at least one compound of a polyamide, a polyester, a polyurethane, or a polyolefin. In the present invention, when the polymer cover layer is formed of a single layer, the single-layer polymer cover layer includes at least one compound of a polyamide, a polyester, a polyurethane, or a polyolefin. Specifically, the polymer cover layer in the present invention includes at least one compound of a polyamide, a polyester, a polyurethane, or a polyolefin on at least the side in contact with the primer layer and preferably includes at least one compound of a polyamide, a polyester, or a polyurethane on the side in contact with the primer layer.

Polyamide

Typical polyamides applicable to a polymer cover layer of a flexible tube for an endoscope can be widely used as the polyamides. Examples thereof include crystalline polyamides, amorphous polyamides, and polyamide elastomers.

Examples of the crystalline polyamides include, but are not particularly limited to, aliphatic polyamides and aromatic polyamides.

Examples of the aliphatic polyamides include poly-ε-caproamide (polyamide 6), polytetramethylene adipamide (polyamide 46), polyhexamethylene adipamide (polyamide 66), polycaproamide/polyhexamethylene adipamide copolymers (polyamide 6/66), polyundecamide (polyamide 11), polycaproamide/polyundecamide copolymers (polyamide 6/11), polydodecamide (polyamide 12), polycaproamide/polydodecamide copolymers (polyamide 6/12), polyhexamethylene sebacamide (polyamide 610), polydecamethylene sebacamide (polyamide 1010), polyhexamethylene dodecamide (polyamide 612), polydecamethylene dodecamide (polyamide 1012), polyundecamethylene adipamide (polyamide 116), and mixtures and copolymers thereof.

Examples of the aromatic polyamides include polyhexamethylene isophthalamide (polyamide 6I), polyhexamethylene terephthalamide (polyamide 6T), polyhexamethylene terephthalamide/polyhexamethylene isophthalamide copolymers (polyamide 6T/6I), polycaproamide/polyhexamethylene terephthalamide copolymers (polyamide 6/6T), polycaproamide/polyhexamethylene isophthalamide copolymers (polyamide 6/6I), polyhexamethylene adipamide/polyhexamethylene terephthalamide copolymers (polyamide 66/6T), polyhexamethylene adipamide/polyhexamethylene isophthalamide copolymers (polyamide 66/6I), polytrimethylhexamethylene terephthalamide (polyamide TMDT), polybis(4-aminocyclohexyl)methane dodecamide (polyamide PACM12), polybis(3-methyl-4-aminocyclohexyl) methane dodecamide (nylon dimethyl PACM12), poly-m-xylylene adipamide (polyamide MXD6), polydecamethylene terephthalamide (polyamide 10T), poly-undecamethylene terephthalamide (polyamide 11T), and mixtures and copolymers thereof.

Examples of the amorphous polyamides include polycondensates of isophthalic acid/terephthalic acid/1,6-hexanediamine/bis(3-methyl-4-aminocyclohexyl)methane, polycondensates of terephthalic acid/2,2,4-trimethyl-1,6-hexanediamine/2,4,4-trimethyl-1,6-hexanediamine, polycondensates of isophthalic acid/bis(3-methyl-4-aminocyclohexyl)methane/ω-laurolactam, polycondensates of isophthalic acid/terephthalic acid/1,6-hexanediamine, polycondensates of isophthalic acid/2,2,4-trimethyl-1,6-hexanediamine/2,4,4-trimethyl-1,6-hexanediamine, polycondensates of isophthalic acid/terephthalic acid/2,2,4-trimethyl-1, 6-hexanediamine/2,4,4-trimethyl-1,6-hexanediamine, polycondensates of isophthalic acid/bis(3-methyl-4-aminocyclohexyl)methane/ω-laurolactam, and polycondensates of isophthalic acid/terephthalic acid/other diamine components.

Examples of the polyamide elastomers include elastomers containing polyamides as hard segments, the elastomers being called amide-based thermoplastic elastomers. Examples thereof include multiblock copolymers having hard segments composed of polyamides and soft segments composed of polyethers or polyesters, and multiblock copolymers having hard segments composed of polyamides and soft segments having bonding forms of both an ether bond and an ester bond. Examples of the hard segments include polyamides 6, 66, 610, 11, and 12. Examples of the polyethers for the soft segments include polyethylene glycol, poly(oxytetramethylene) glycol, and poly(oxypropylene) glycol. Examples of the polyesters in the soft segments include poly(ethylene adipate)glycol and poly(butylene-1,4-adipate)glycol.

Examples of commercially available polyamides that can be used in the present invention include polyamide 11 (trade name "Rilsan BMN 0" manufactured by Arkema Inc.), polyamide 12 (trade name "DAIAMID L1940" manufactured by Daicel-Evonik Ltd.), polyamide 1010 (trade name "VESTAMID Terra DS16" manufactured by Daicel-Evonik Ltd.), polyamide 1012 (trade name "VESTAMID Terra DD16" manufactured by Evonik), an amorphous polyamide (trade name "TROGAMID CX7323" manufactured by Daicel-Evonik Ltd.), and polyamide elastomers (trade names "Pebax 4533", "Pebax 7233", and "Pebax Rnew 80R53" manufactured by Arkema Inc.).

These polyamides may be used alone or in combination of two or more thereof.

Polyester

Typical polyesters applicable to a polymer cover layer of a flexible tube for an endoscope can be widely used as the polyesters. Examples thereof include thermoplastic polyesters and polyester elastomers.

Examples of the thermoplastic polyesters include polyester resins formed from a dicarboxylic acid component and a diol component and polyester resins formed from a hydroxycarboxylic acid component.

Examples of the dicarboxylic acid component include terephthalic acid, isophthalic acid, phthalic acid, 2,6-naphthalenedicarboxylic acid, 4,4'-biphenyldicarboxylic acid, sodium 5-sulfoisophthalate, oxalic acid, succinic acid, adipic acid, sebacic acid, azelaic acid, dodecanedioic acid, dimer acids, maleic anhydride, maleic acid, fumaric acid, itaconic acid, citraconic acid, mesaconic acid, and cyclohexanedicarboxylic acid.

Examples of the diol component include ethylene glycol, diethylene glycol, 1,3-propanediol, 1,4-butanediol, neopentyl glycol, 1,6-hexanediol, cyclohexanedimethanol, triethylene glycol, polyethylene glycol, polypropylene glycol, polytetramethylene glycol, and ethylene oxide adducts of bisphenol A and bisphenol S.

Examples of the hydroxycarboxylic acid component include ε-caprolactone, lactic acid, and 4-hydroxybenzoic acid.

The thermoplastic polyester resins may be homopolymers formed from the dicarboxylic acid component and the diol component or homopolymers formed from the hydroxycarboxylic acid component, or copolymers formed from the above components. The thermoplastic polyester resins may further contain a small amount of a trifunctional or higher compound component such as trimellitic acid, trimesic acid, pyromellitic acid, trimethylolpropane, glycerin, or pentaerythritol.

Examples of the polyester elastomers include elastomers containing polyesters as hard segments, the elastomers being called ester-based thermoplastic elastomers. Examples thereof include multiblock copolymers having hard segments composed of crystalline polyesters and soft segments composed of polyethers or polyesters, and multiblock copolymers having hard segments composed of crystalline polyesters and soft segments having bonding forms of both an ether bond and an ester bond.

Examples of the hard segments include polybutylene terephthalate and polyethylene terephthalate.

Examples of the soft segments include polyalkylene glycols such as polytetramethylene glycol and polypropylene glycol, bisphenol A-ethylene oxide adducts, bisphenol A-propylene oxide adducts, and polyesters such as polycaprolactone.

For example, block copolymers composed of high-melting-point polyester segments (hard segments) and low-melting-point polymer segments (soft segments) having a molecular weight of 400 to 6,000 can be used as the polyester elastomers, as described in, for example, JP1999-92636A (JP-H11-92636A).

Examples of commercially available polyesters used in the present invention include polyester elastomers (trade names "PELPRENE P-40B", "PELPRENE P-70B", and "PELPRENE S-3001" manufactured by Toyobo Co., Ltd. and trade name "PRIMALLOY B1942" manufactured by Mitsubishi Chemical Corporation) and polybutylene terephthalate (trade name "NOVADURAN 5505S" manufactured by Mitsubishi Engineering-Plastics Corporation).

These polyesters may be used alone or in combination of two or more thereof.

Polyurethane

Typical polyurethanes applicable to a polymer cover layer of a flexible tube for an endoscope can be widely used as the polyurethanes. For example, carbonate-based, ether-based, or ester-based polyurethanes, or mixed polyurethanes of these can be used. Polyurethane elastomers are also preferred. The polyurethane elastomers may be block polymers including hard segments composed of polyurethanes and soft segments having an ether, ester, or carbonate bond or a mixed form of these bonds, the block polymers being called urethane-based thermoplastic elastomers. Such polyurethane elastomers can be appropriately prepared depending on the purpose. Examples thereof include block polymers including hard segments composed of low-molecular-weight glycol components and diisocyanate components and soft segments composed of high-molecular-weight (long-chain) diol components and diisocyanate components.

Examples of the high-molecular-weight (long-chain) diol components include polyether diols, polyester diols, and lactone-based polyester diols. Examples thereof include polypropylene glycol, polytetramethylene oxide, poly(1,4-butylene adipate), poly(ethylene adipate-co-1,4-butylene adipate), polycaprolactone-based diol, poly(1,6-hexylene carbonate), and poly(1,6-hexylene adipate-co-neopentylene adipate). The high-molecular-weight (long-chain) diols preferably have a number-average molecular weight of 500 to 10,000.

As the low-molecular-weight glycol components, short-chain diols such as ethylene glycol, propylene glycol, 1,4-butanediol, and bisphenol A can be used. The short-chain diols preferably have a number-average molecular weight of 48 to 500.

Examples of the diisocyanate components include diphenylmethane diisocyanate, hexamethylene diisocyanate, tolidine diisocyanate, 1,5-naphthalene diisocyanate, isophorone diisocyanate, and xylylene diisocyanate.

For the polyurethane elastomers according to the above embodiment, the disclosure of, for example, JP2005-015643A can be referred to.

Examples of commercially available polyurethanes that can be used in the present invention include PANDEX T-2185 and T-2983N (which are manufactured by DIC Corporation), Miractran (manufactured by Nippon Miractran Co., Ltd.), Elastollan (manufactured by BASF Japan Ltd.), RESAMINE (manufactured by Dainichiseika Color & Chemicals Mfg. Co., Ltd.), Pellethane (manufactured by Dow Chemical Japan Ltd.), Iron Rubber (manufactured by NOK Corporation), and Mobilon (manufactured by Nisshinbo Chemical Inc.). Examples thereof further include Isoplast (manufactured by Lubrizol Corporation), Tecoflex (manufactured by Lubrizol Corporation), Superflex 830, 460, 870, 420, and 420NS (polyurethanes manufactured by DKS Co., Ltd.), Hydran AP-40F, WLS-202, and HW-140SF (polyurethanes manufactured by DIC Corporation), Olester UD500 and UD350 (polyurethanes manufactured by Mitsui Chemicals, Inc.), and Takelac W-615, W-6010, W-6020, W-6061, W-405, W-5030, W-5661, W-512A-6, W-635, and WPB-6601 (manufactured by Mitsui Chemicals, Inc.).

These polyurethanes may be used alone or in combination of two or more thereof.

Polyolefin

Typical polyolefins applicable to a polymer cover layer of a flexible tube for an endoscope can be widely used as the polyolefins. Examples thereof include polyolefin resins and rubbers, and olefin-based elastomers.

Examples of the polyolefin resins and rubbers include homopolymers and copolymers of α-olefins having 2 to 20 carbon atoms, such as ethylene, propylene, 1-butene, 1-hexene, and 4-methyl-pentene. Examples thereof further include copolymers of α-olefins and nonconjugated dienes having 2 to 20 carbon atoms, such as dicyclopentadiene, 1,4-hexadiene, cyclooctadiene, methylene norbornene, ethylidene norbornene, butadiene, and isoprene. Examples thereof further include ethylene-α-olefin copolymer rubbers, ethylene-α-olefin-nonconjugated diene copolymer rubbers, propylene-α-olefin copolymer rubbers, and butene-α-olefin copolymer rubbers. It is also possible to use, for example, ethylene-(meth)acrylic acid copolymers, ethylene-(meth) acrylic acid ester-(meth)acrylic acid copolymers, ethylene-vinyl acetate copolymers, ethylene-vinyl acetate-(meth) acrylic acid copolymers, ethylene-propylene-(meth)acrylic acid copolymers, ethylene-propylene-(meth)acrylic acid ester-(meth)acrylic acid copolymers, ethylene-maleic anhydride copolymers, ethylene-(meth)acrylic acid ester-maleic anhydride copolymers, ethylene-butene-maleic anhydride copolymers, ethylene-butene-(meth)acrylic acid copolymers, ethylene-butene-maleic anhydride-(meth)acrylic acid copolymers, propylene-butene-maleic anhydride copolymers, propylene-butene-(meth)acrylic acid copolymers, propylene-butene-maleic anhydride-(meth)acrylic acid copolymers, and ethylene-vinyl chloride copolymers.

Examples of polyolefins in the olefin-based elastomers include ethylene-propylene copolymers, ethylene-1-butene copolymers, ethylene-α-olefin copolymers, propylene-1-butene copolymers, propylene-α-olefin copolymers, 1-butene-α-olefin copolymers, propylene-1-butene-ethylene copolymers, propylene-α-olefin-ethylene copolymers, propylene-α-olefin-1-butene copolymers, 1-butene-α-olefin-ethylene copolymers, and polypropylene.

Examples of rubber components in the olefin-based elastomers include propylene rubber (PP), ethylene-propylene rubber (EPM), ethylene-propylene-diene rubber (EPDM), polyisoprene, polybutadiene, polychloroprene, and isobutylene-isoprene copolymers.

The olefin-based elastomers may contain one of the polyolefins alone or two or more of the polyolefins and may contain one of the rubber components alone or two or more of the rubber components.

Examples of commercially available polyolefins used in the present invention include "SARLINK 3145D" (trade name, manufactured by Toyobo Co., Ltd.) and Zelas MC707 (trade name, manufactured by Mitsubishi Chemical Corporation).

These polyolefins may be used alone or in combination of two or more thereof.

The total amount of compounds selected from the group consisting of polyamides, polyesters, polyurethanes, and polyolefins contained in the polymer cover layer in the case of a single-layer polymer cover layer, and the total amount of compounds selected from the group consisting of polyamides, polyesters, polyurethanes, and polyolefins contained in the innermost layer in the case of a multilayer polymer cover layer are each preferably 50% by mass or more, more preferably 70% by mass or more, still more preferably 80% by mass or more, and even more preferably 90% by mass or more. When the polymer cover layer is formed of a single layer, the polymer cover layer may be a layer composed of at least one compound of a polyamide, a polyester, a polyurethane, or a polyolefin. When the polymer cover layer is formed of a plurality of layers, the innermost layer may be a layer composed of at least one compound of a polyamide, a polyester, a polyurethane, or a polyolefin.

When the polymer cover layer in the case of a single-layer polymer cover layer and the innermost layer in the case of a multilayer polymer cover layer include a polymer other than polymers selected from the group consisting of polyamides, polyesters, polyurethanes, and polyolefins, the polymer is not particularly limited as long as the effects of the present invention are not impaired.

The polymer cover layer may appropriately contain various common additives as long as the effects of the present invention are not impaired. Examples of the additives include a heat-resistant stabilizer, a mineral filler, an impact resistance-improving agent, a plasticizer, a lubricant, a metal soap, a light-fast auxiliary agent, and a colorant. The amounts of the additives contained in the polymer cover layer can also be appropriately adjusted. Such additives may be derived from polymer materials used or can be added separately from polymers.

When the polymer cover layer is formed of a plurality of layers, a layer other than the innermost layer also preferably includes at least one compound of a polyamide, a polyester, a polyurethane, or a polyolefin. A layer having desired physical properties can be formed by appropriately combining these polymers.

Each of the polymers that can be used as the polymer cover layer according to the present invention preferably has a molecular weight of 10,000 to 1,000,000, more preferably has a molecular weight of 20,000 to 500,000, and particularly preferably has a molecular weight of 30,000 to 300,000.

In the present invention, the molecular weight of the polymer that forms the polymer cover layer means a weight-average molecular weight unless otherwise noted. The weight-average molecular weight can be measured by gel permeation chromatography (GPC) as a molecular weight in terms of polystyrene.

As illustrated in FIG. 2, the polymer cover layer 15 in the present invention is preferably formed so as to have a substantially uniform thickness in the longitudinal direction (axial direction) of the flexible-tube base 14. The polymer cover layer 15 has a thickness of, for example, 0.2 mm to 1.0 mm. An outer diameter D of the flexible tube 3a is appropriately determined according to the purpose. The outer diameter D is, for example, 11 to 14 mm. In FIG. 2, the inner layer 17 and the outer layer 18 are formed such that the proportions of the thicknesses of the layers 17 and 18 relative to the total thickness of the polymer cover layer 15 change in the axial direction of the flexible-tube base 14. Specifically, on one end 14a side (distal end side) of the flexible-tube base 14 to be attached to the angle portion 3b, the thickness of the inner layer 17 is larger than the thickness of the outer layer 18 with respect to the total thickness of the polymer cover layer 15. The thickness of the inner layer 17 gradually decreases from the one end 14*a* toward the other end 14*b* side (proximal end side) to be attached to the main-body operation section 5. On the other end 14*b* side, the thickness of the outer layer 18 is larger than the thickness of the inner layer 17.

In FIG. 2, the proportion of the thickness of the inner layer 17 is maximum at the one end 14*a*, and the proportion of the thickness of the outer layer 18 is maximum at the other end 14*b*. The proportion of the thickness of the inner layer 17 to the thickness of the outer layer 18 may be, for example, 9:1 at the one end 14*a* and may be, for example, 1:9 at the other end 14*b*. The thicknesses of the two layers are changed such that the proportion of the thickness of the inner layer 17 to the thickness of the outer layer 18 is reversed from the end 14*a* to the end 14*b*. With this configuration, the flexible tube 3*a* has a difference in hardness between the one end 14*a* side and the other end 14*b* side, and flexibility can be changed in the axial direction such that the one end 14*a* side is soft and the other end 14*b* side is hard. The proportion of the thickness of the inner layer to the thickness of the outer layer is preferably 95:5 to 60:40 (inner layer:outer layer) at the one end and is preferably 5:95 to 40:60 (inner layer:outer layer) at the other end.

When the proportion of the thickness of the inner layer 17 to the thickness of the outer layer 18 is within the range of 95:5 to 5:95, the amount of extrusion of a polymer that forms a layer having a smaller thickness can also be accurately controlled.

The soft polymer used in the inner layer 17 and the hard polymer used in the outer layer 18 preferably have a difference in 100% modulus, which is an indicator indicating a hardness after molding, of 1 MPa or more and more preferably 3 MPa or more. The difference in melt viscosity, which is an indicator indicating a fluidity of a polymer in a molten state, at a molding temperature of 150° C. to 300° C. is preferably 2,500 Pa·s or less. With this configuration, the polymer cover layer 15 composed of the inner layer 17 and the outer layer 18 is reliably provided with both good molding accuracy and the required difference in hardness between the distal end side and the proximal end side.

Topcoat Layer

In the flexible tube according to the present invention, the topcoat layer 16 is disposed on an outer periphery of the polymer cover layer 15 as needed. Examples of materials that can be applied to the topcoat layer include, but are not particularly limited to, urethane coatings, acrylic coatings, fluorine coatings, silicone coatings, epoxy coatings, and polyester coatings.

Main purposes of use of the topcoat layer are to protect the surface of the flexible tube or make the surface glossy, to impart slidability, and to impart chemical resistance. Therefore, the topcoat layer preferably has a high modulus of elasticity, a smooth surface, and good chemical resistance.

Method for Producing Flexible Tube

Formation of Siloxane Compound-Containing Layer

Specific examples of the method for forming a siloxane compound-containing layer will be described below, but the present invention is not limited to these.

A siloxane compound-containing layer can be formed on (the outer periphery of) a flexible-tube base through the following steps (i) and (ii).

(i) An alkoxysilane compound is subjected to a dehydration condensation reaction to prepare a silica composition.

(ii) After the silica composition is applied onto a flexible-tube base, the silica composition is dried (or heated) to form a coating film, followed by heating.

In the step (i), in a composition containing an alkoxysilane compound, water, and an organic solvent, the alkoxysilane compound is subjected to a dehydration condensation reaction to obtain a silica composition.

For example, an alkoxysilane compound, an organic solvent, and water are mixed, a catalyst described later is blended as required, and the mixture is mixed, for example, at 40° C. to 120° C. for ten minutes to eight hours. An organic solvent (preferably, the same organic solvent as the above organic solvent) is added to the resulting mixture, and the mixture is stirred at room temperature (for example, 25° C. to 30° C.) for about 10 to 90 minutes to prepare a homogeneous solution. The solution prepared as described above is diluted with an organic solvent (preferably, an organic solvent different from the above organic solvent).

The content of silane compounds (silicon atom-containing compounds) in the silica composition is preferably 0.05% by mass or more, more preferably 0.1% by mass or more, still more preferably 0.5% by mass or more, and even more preferably 1% by mass or more, in total. On the other hand, the content of the silane compounds is preferably 70% by mass or less, more preferably 50% by mass or less, still more preferably 40% by mass or less, and even more preferably 20% by mass or less, in total.

The silica composition may contain a surfactant in order to make the siloxane compound-containing layer porous.

Organic solvents in which the above-described alkoxysilane compound and water can be mixed are preferably used as the organic solvents. Specifically, water-soluble organic solvents are preferred. Examples thereof include alcohol compounds such as monohydric alcohols having 1 to 5 carbon atoms, e.g., methanol, ethanol, 1-propanol, 2-propanol, 2-methyl-1-propanol, 1-butanol, 2-butanol, t-butanol, and 1-pentanol, dihydric alcohols having 1 to 4 carbon atoms, and polyhydric alcohols, e.g., glycerin and pentaerythritol; etherified products and esterified products of the above alcohol compounds, such as methyl acetate, ethyl acetate, isobutyl acetate, diethylene glycol, ethylene glycol monomethyl ether, ethylene glycol dimethyl ether, 2-ethoxyethanol, propylene glycol monomethyl ether, and propylene glycol methyl ether acetate; ketone compounds such as acetone and methyl ethyl ketone; amide compounds such as formamide, N-methylformamide, N-ethylformamide, N,N-dimethylformamide, N,N-diethylformamide, N-methylacetamide, N-ethylacetamide, N,N-dimethylacetamide, N,N-diethylacetamide, N-methylpyrrolidone, N-formylmorpholine, N-acetylmorpholine, N-formylpiperidine, N-acetylpiperidine, N-formylpyrrolidine, N-acetylpyrrolidine, N,N'-diformylpiperazine, and N,N'-diacetylpiperazine; lactone compounds such as y-butyrolactone; ureas such as tetramethylurea and N,N'-dimethylimidazolidine; and dimethyl sulfoxide. Of these, alcohols are preferred, and monohydric alcohols are more preferred in order to hydrolyze the contained alkoxysilane compound under more stable conditions.

The silica composition usually contains a catalyst. Any substance that promotes the hydrolysis and dehydration condensation reaction of the alkoxysilane compound may be used as the catalyst.

Examples thereof include acids such as hydrofluoric acid, phosphoric acid, boric acid, hydrochloric acid, nitric acid, sulfuric acid, formic acid, acetic acid, oxalic acid, maleic acid, methylmalonic acid, stearic acid, linoleic acid, benzoic acid, phthalic acid, citric acid, and succinic acid; amine compounds such as ammonia, butylamine, dibutylamine, and triethylamine; bases such as pyridine; and Lewis acids such as an acetylacetone complex of aluminum.

Examples of the catalyst further include metal chelate compounds. Examples of the metal species in the metal chelate compounds include titanium, aluminum, zirconium, tin, and antimony.

The silica composition may contain components other than the alkoxysilane compound, the organic solvent, the surfactant, water, and the catalyst as long as the effects of the present invention are not impaired.

In the step (ii), for example, a flexible-tube base is immersed in the silica composition obtained in the step (i), and the flexible-tube base is then taken out and dried to form a coating film. Subsequently, heating is performed at 80° C. to 400° C. Thus, a flexible-tube base having a siloxane compound-containing layer can be obtained.

When a commercially available siloxane compound is used, a silica composition including the siloxane compound in an amount of, for example, 0.01% to 3% by mass in the organic solvent is prepared, and the step (ii) can be performed using this composition.

Prior to the formation of the siloxane compound-containing layer, the flexible-tube base is preferably cleaned by degreasing with an acid solution, an alkali solution, an aqueous solution of a surfactant, an organic solvent, or the like. After the cleaning, the flexible-tube base is preferably further cleaned with water or hot water so that the amount of an acid, an alkali, a surfactant, or the like decreases from the surface of the base.

In the present invention, a portion that is not covered with the siloxane compound-containing layer may be present on the flexible-tube base (that is, a portion of the siloxane compound-containing layer may have a void) as long as the effects of the present invention are not impaired.

Formation of Primer Layer

In the production of the flexible tube according to the present invention, after the siloxane compound-containing layer is formed, a primer layer is formed on the siloxane compound-containing layer. The primer layer can be formed by dissolving at least one of a silane coupling agent, a titanium coupling agent, a zirconium coupling agent, or an aluminum coupling agent in a solvent to prepare a coating liquid; forming a coating film on at least the outer periphery of the flexible-tube base by, for example, applying or spraying the coating liquid onto the outer periphery of the flexible-tube base or immersing the flexible-tube base into the coating liquid; and subsequently drying the coating film by an ordinary method (for example, drying at a high temperature of about 100° C.).

Examples of the solvent that can be used in the coating liquid include alcohol solvents such as methanol and ethanol; ketone solvents such as acetone and methyl ethyl ketone; ester solvents such as ethyl acetate; hydrocarbon solvents such as toluene; and liquid mixtures thereof. It is preferable to further mix water or an acid catalyst such as acetic acid with the solvents in order to accelerate hydrolysis of the silane coupling agent, the titanium coupling agent, the zirconium coupling agent, and the aluminum coupling agent. The coating liquid may be prepared to be acidic (for example, pH 1 to 4 at 25° C.) or alkaline (for example, pH 9 to 11 at 25° C.).

The content of the silane coupling agent, the titanium coupling agent, the zirconium coupling agent, and the aluminum coupling agent in the coating liquid is not particularly limited. For example, the content may be 0.01% to 2% by mass and is preferably 0.05% by mass or more and less than 1.5% by mass, and more preferably 0.1% by mass or more and less than 1.0% by mass, in total.

The coating liquid may include, for example, a surfactant and a catalyst in addition to at least one of a silane coupling agent, a titanium coupling agent, a zirconium coupling agent, or an aluminum coupling agent, a solvent, and a pH adjuster. The coating liquid is more preferably composed of at least one of a silane coupling agent, a titanium coupling agent, a zirconium coupling agent, or an aluminum coupling agent, and a solvent.

In the present invention, a portion that is not covered with the primer layer may be present on the siloxane compound-containing layer (that is, a portion of the primer layer may have a void) as long as the effects of the present invention are not impaired.

Formation of Polymer Cover Layer

Formation of a polymer cover layer will be described by taking, as an example, a case where the polymer cover layer has a two-layer structure.

A flexible tube that includes a polymer cover layer having a two-layer structure composed of an inner layer and an outer layer can be produced by, for example, melt-kneading and extruding, around the flexible-tube base on which the primer layer has been formed, a first polymer material (a polymer material including at least one compound of a polyamide, a polyester, a polyurethane, or a polyolefin) that constitutes the inner layer and a second polymer material that constitutes the outer layer to cover the flexible-tube base.

In an embodiment in which a polymer cover layer is formed of one layer or three or more layers, the polymer cover layer can also be obtained by appropriately changing the layer configuration with reference to the method described below.

Figure 3:
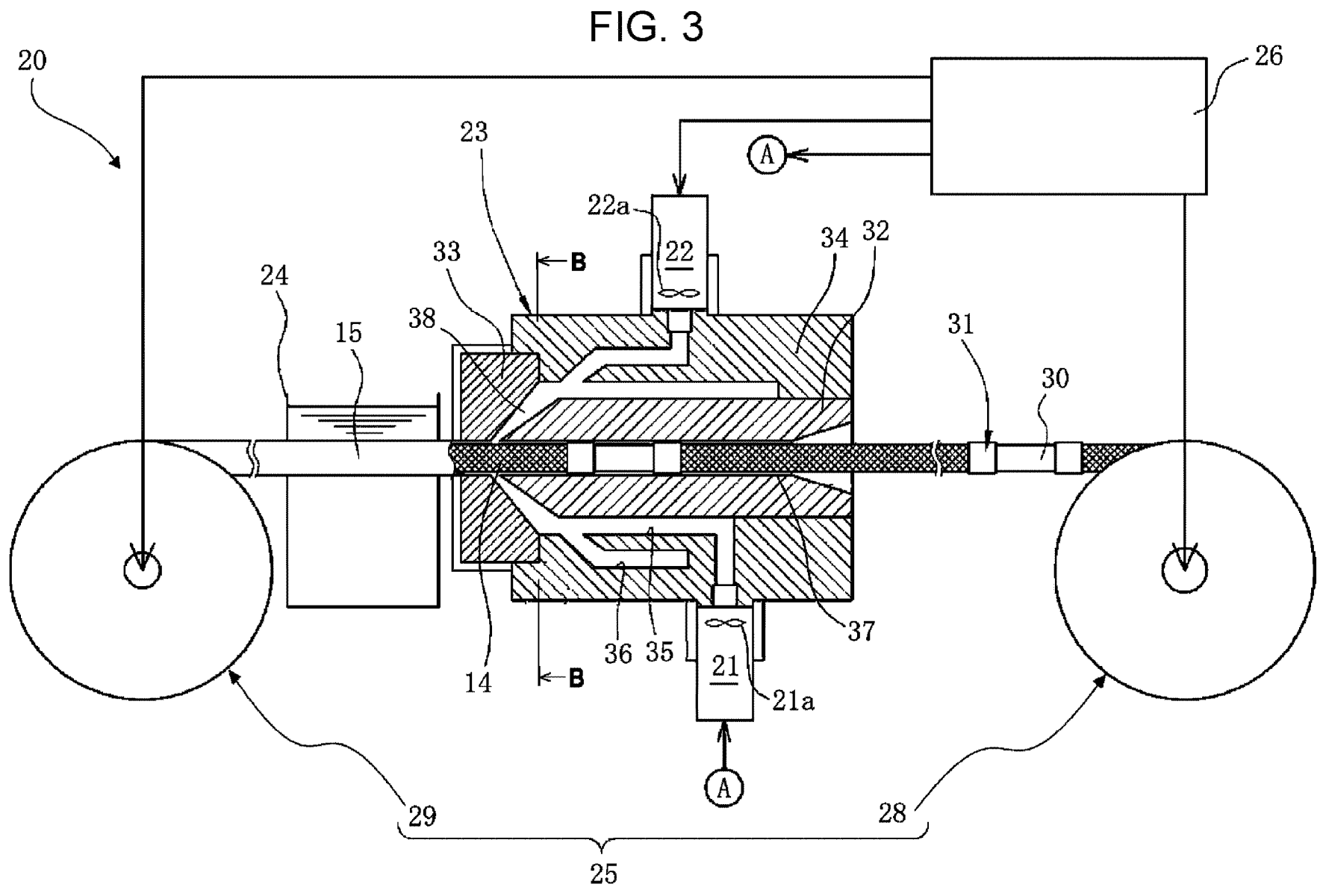
Figure 4:
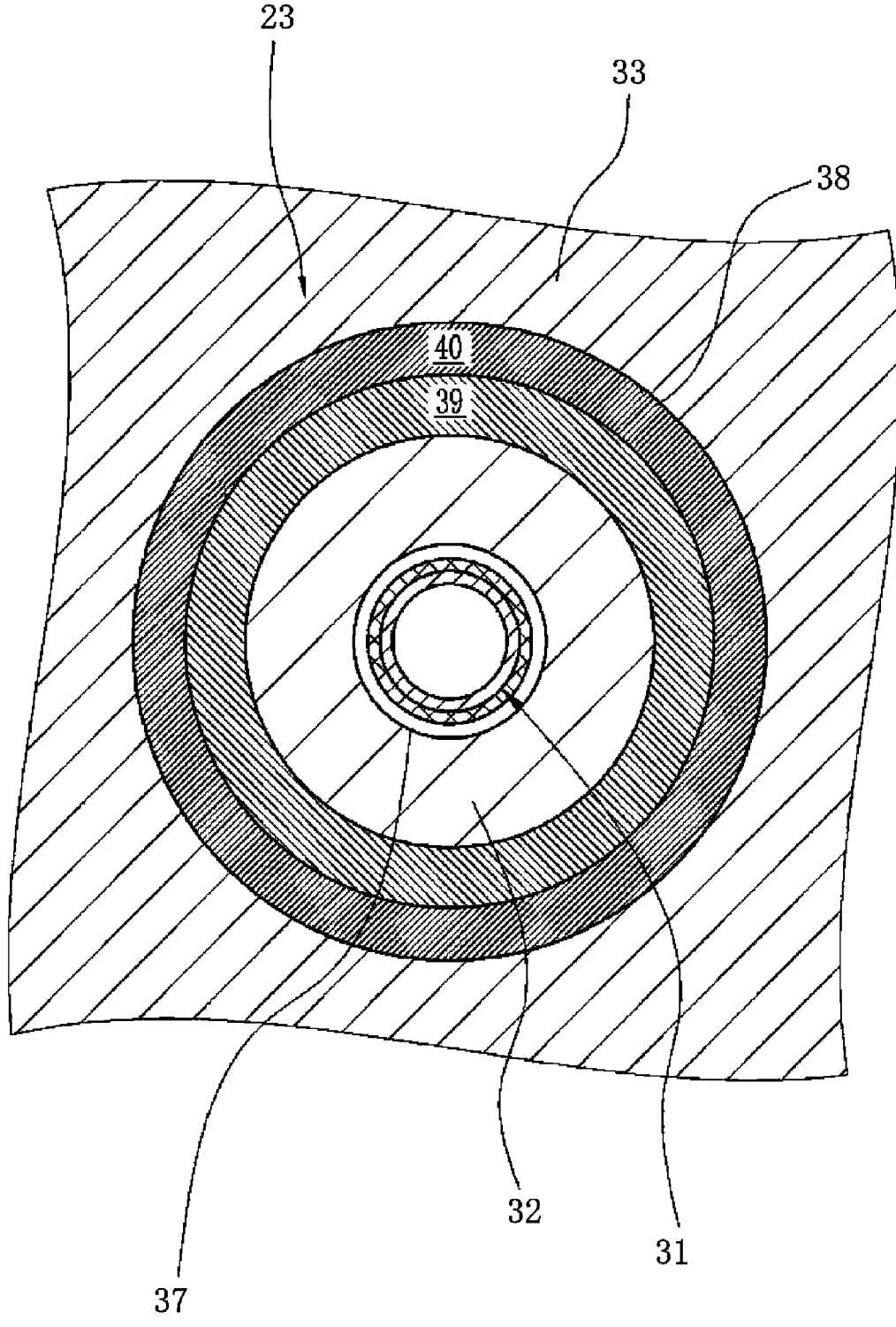
FIG. 4 is a sectional view taken along line B-B in FIG. 3.

An example of a method for forming a polymer cover layer of the flexible tube 3a (FIGS. 1 and 2) will be described with reference to FIGS. 3 and 4. In this embodiment, a continuous molding machine is used to mold a polymer cover layer 15. It is preferable to use a continuous molding machine 20 that includes well-known extrusion units 21 and 22 including hoppers, screws 21a and 22a, etc.; a head unit 23 configured to mold a polymer cover layer 15 so as to cover an outer peripheral surface of a flexible-tube base 14; a cooling unit 24; a transport unit 25 (including a feed drum 28 and a take-up drum 29) configured to transport a connected flexible-tube base 31 to the head unit 23; and a control unit 26 configured to control the above units. The head unit 23 preferably includes a nipple 32, a die 33, and a support 34 configured to fixedly support the nipple 32 and the die 33. For example, the apparatus disclosed in FIGS. 3 to 5 of JP2011-72391A can be used as an example of the apparatus having the above configuration.

The inside of the die 33 is preferably heated to a predetermined molding temperature. The molding temperature is preferably set in a range of 150° C. to 300° C. The temperatures of a first polymer material 39 and a second polymer material 40 can be increased by controlling the temperatures of a heating unit in the apparatus by heating. In addition to this, as the rotational speeds of the screws 21a and 22a become higher, the temperatures of the first polymer material 39 and the second polymer material 40 can be further increased to increase their fluidity. During this process, the molding thicknesses of the inner layer 17 and the outer layer 18 can be adjusted by changing the amounts of the molten first polymer material 39 and second polymer material 40 ejected while the transport speed of the connected flexible-tube base 31 is made constant.

The process of molding the polymer cover layer 15 on the connected flexible-tube base 31 by the continuous molding machine 20 will be described. When the continuous molding machine 20 performs a molding step, the molten first polymer material 39 and second polymer material 40 are respectively extruded from the extrusion units 21 and 22 into the head unit 23. At the same time, the transport unit 25 operates so that the connected flexible-tube base 31 is transported to the head unit 23. During this process, the extrusion units 21 and 22 are in a state of constantly extruding the first polymer material 39 and the second polymer material 40 to feed the polymer materials 39 and 40 to the head unit 23, and the first polymer material 39 and the second polymer material 40 that are respectively extruded from the extrusion units 21 and 22 to gates 35 and 36 pass through an edge and join to each other, and are fed, in a stacked state, through a polymer passage 38 to a molding passage 37. As a result, a two-layer molded polymer cover layer 15 is formed in which an inner layer 17 using the first polymer material 39 and an outer layer 18 using the second polymer material 40 are stacked.

The connected flexible-tube base 31 includes a plurality of flexible-tube bases 14 (having a siloxane compound-containing layer and a primer layer on the outer peripheries of the flexible-tube bases 14) that are connected together. While the connected flexible-tube base 31 is transported through the molding passage 37, the polymer cover layer 15 is continuously molded on the plurality of flexible-tube bases 14. When the polymer cover layer 15 is molded from one end 14a side (distal end side) of one flexible-tube base to the other end 14b side (proximal end side) thereof, the thickness of the inner layer 17 is made large immediately after the extrusion units 21 and 22 start the ejection of the polymers. The proportion of the thickness of the outer layer 18 is then gradually increased over an intermediate portion toward the other end 14b side. It is preferable to control the amounts of the polymers ejected in this manner such that the polymer cover layer 15 has the gradient thickness proportion described above.

Joint members 30 each function as a connecting portion of two flexible-tube bases 14, and thus the control unit 26 is used to switch the amounts of the polymers ejected from the extrusion units 21 and 22. Specifically, the control unit 26 preferably switches the amounts of the polymers ejected from the extrusion units 21 and 22 such that the thickness proportion changes from a thickness proportion on the other end 14b side (proximal end side) of one flexible-tube base 14 to a thickness proportion on one end 14a side (distal end side) of the next flexible-tube base 14. When the polymer cover layer 15 is molded from the one end 14a side of the next flexible-tube base 14 to the other end 14b side thereof, the extrusion units 21 and 22 are preferably similarly controlled such that the thickness of the outer layer gradually increases from the one end side toward the other end side.

The connected flexible-tube base 31 on which the polymer cover layer 15 is molded to the rearmost end is removed from the continuous molding machine 20, and the joint members 30 are then removed from the flexible-tube bases 14 to separate the flexible-tube bases 14 from each other. Next, for each of the separated flexible-tube bases 14, the polymer cover layer 15 is coated with the topcoat layer 16 to complete flexible tubes 3a. The completed flexible tubes 3a are transported to an assembly step of an electronic endoscope.

In the present invention, when the polymer cover layer is formed of a plurality of layers, a functional layer may be disposed between layers constituting the plurality of layers.

The above description has been made with reference to the drawings by taking, as an example, an electronic endoscope configured to observe an image of the condition of a subject picked up with an imaging device; however, the present invention is not limited to this and is also applicable to an endoscope configured to observe the condition of a subject by using an optical image guide.

The flexible tube according to the present invention is widely applicable to endoscopic medical devices. For example, the flexible tube according to the present invention is applicable to an endoscope equipped with a clip or wire at the distal end thereof or to a device equipped with a basket or brush. Note that the term "endoscopic medical device" is meant to broadly include medical devices or diagnosis and treatment devices that include an insertion section having flexibility and that are introduced and used in the body, such as remote-controlled medical devices, in addition to medical devices including an endoscope as a basic structure, as described above.

An endoscopic medical device according to the present invention has an insertion section in which the flexible tube for an endoscope according to the present invention is incorporated. That is, a method for producing an endoscopic medical device according to the present invention includes incorporating the flexible tube for an endoscope according to the present invention into an insertion section of an endoscopic medical device.

EXAMPLES

Hereinafter, the present invention will be described in more detail by way of Examples; however, these Examples should not be construed as limiting the present invention.
Production of Flexible-Tube for Endoscope Flexible tubes having the structure illustrated in FIG. 2 were produced. The polymer cover layer had a single-layer structure or a two-layer structure as shown in Table 2 below.
Flexible-Tube Base Flexible-tube bases were each prepared by forming a spiral tube 11 using a metal strip 11a made of stainless steel (SUS304), and covering the spiral tube 11 with a tubular mesh member 12 obtained by weaving fibers made of SUS304. The flexible-tube bases have a length of 80 cm and a diameter of 12 mm. The stainless steel flexible tube bases each have a passivation layer on a surface thereof, the passivation layer being formed by annealing treatment (heating treatment) during the formation of the spiral tube and the tubular mesh member.

The flexible-tube bases were cleaned by degreasing with acetone and then immersing in a 1 N aqueous sodium hydroxide solution at 50° C. for three minutes. Subsequently, rinsing was performed with distilled water three times, and drying was then performed in an oven heated to 100° C. for 10 minutes to prepare flexible-tube bases.
Formation of Siloxane Compound-Containing Layer (L-1)

Twenty grams of tetraethoxysilane, 20 g of methyltriethoxysilane, 9 g of ethanol, 14 g of water, and 33 g of a 0.3 mass % aqueous hydrochloric acid solution were mixed, and the mixture was stirred in a water bath at 63° C. for 30 minutes and then further stirred at room temperature for 30 minutes to prepare a mixture (A).

The mixture (A) was mixed with 15 g of a nonionic surfactant (polyethylene oxide-polypropylene oxide-polyethylene oxide-triblock polymer, "PLURONIC P-123 (trade name)" manufactured by BASF, number-average molecular weight: 5,800) and 12 g of ethanol, and the mixture was stirred at room temperature for 60 minutes to prepare a mixture (B).

The mixture (B) was diluted 25 times with 1-butanol and filtered through a filter with a mesh size of 0.45 μm to obtain a silica composition (C) (solid content: 1.0%).

The flexible-tube base after cleaning was immersed in the epoxy resin solution (E) for five minutes, then pulled up, and air-dried at 40° C. for 30 minutes to volatilize the methyl ethyl ketone. The flexible-tube base was heated in an oven at 100° C. for three hours to form an epoxy resin layer (R-1) on the outer periphery of the flexible-tube base. The epoxy resin layer (R-1) has an average layer thickness of 80 nm.

TABLE 1

| | Siloxane compound-containing layer | | | | | | | | |
| | (L-2) | (L-3) | (L-4) | (L-5) | (L-6) | (L-7) | (L-8) | (L-9) | (L-10) |
|---|---|---|---|---|---|---|---|---|---|
| N-103X | 20 g | 50 g | 100 g | 250 g | 500 g | 1000 g | | | |
| HAS-10 | | | | | | | 500 g | 750 g | 1000 g |
| Ethanol | 980 g | 950 g | 900 g | 750 g | 500 g | | 500 g | 250 g | |
| Solid content (%) | 0.04% | 0.10% | 0.20% | 0.50% | 1.0% | 2.0% | 5.0% | 7.5% | 10.0% |
| Average layer thickness | 10 nm | 20 nm | 30 nm | 50 nm | 80 nm | 120 nm | 180 nm | 260 nm | 360 nm |

Notes in Table 1
N-103X: Hydrolyzed silicate ("N-103X" (trade name), manufactured by Nippon Colcoat Co., Ltd., solid content: 2.0% by mass, isopropyl alcohol/n-butanol solvent, being in a hydrolyzed state and having a hydroxy group)
HAS-10: Hydrolyzed silicate ("HAS-10" (trade name) manufactured by Nippon Colcoat Co., Ltd., solid content: 10.2% by mass, methanol/isopropyl alcohol/ethanol solvent, being in a hydrolyzed state and having a hydroxy group)

The flexible-tube base after cleaning was immersed in the silica composition (C) for five minutes, then pulled up, and air-dried at 40° C. for 30 minutes. The flexible-tube base was heated in an oven at 300° C. for five minutes to remove the nonionic surfactant by thermal decomposition, thereby forming a siloxane compound-containing layer (L-1) on the outer periphery of the flexible-tube base. The siloxane compound-containing layer (L-1) has a porous structure and has an average layer thickness of 50 nm. This siloxane compound-containing layer (L-1) has hydroxy groups.

Formation of Siloxane Compound-Containing Layer (L-2)

Twenty grams of a hydrolyzed silicate ("N-103X" (trade name), manufactured by Nippon Colcoat Co., Ltd., solid content: 2.0% by mass, isopropyl alcohol/n-butanol solvent) was diluted with 980 g of ethanol to prepare a silica composition (D) (solid content: 0.04%). The flexible-tube base after cleaning was immersed in the silica composition (D) for one minute, then pulled up, and air-dried at 30° C. for 30 minutes. The flexible-tube base after air-drying was heated in an oven at 100° C. for 15 minutes to form a siloxane compound-containing layer (L-2) on the outer periphery of the flexible-tube base.

Formation of Siloxane Compound-Containing Layers (L-3) to (L-10)

Siloxane compound-containing layers (L-3) to (L-10) were formed on the outer peripheries of the flexible-tube bases as in the siloxane compound-containing layer (L-2) except that the components shown in Table 1 below were used. Specifically, flexible-tube bases having the siloxane compound-containing layers (L-3) to (L-10) on the outer peripheries thereof were obtained. These siloxane compound-containing layers (L-3) to (L-10) have hydroxy groups.

Formation of Epoxy Resin Layer (R-1)

In a stainless steel vessel, 6.0 g of a bisphenol A-type epoxy resin ("jER828" (trade name), manufactured by Mitsubishi Chemical Corporation, epoxy equivalent: 184 to 194 g/eq.) and 990 g of methyl ethyl ketone were mixed, 4.0 g of 1,6-diaminohexane was further added to the mixture, and the mixture was then stirred at room temperature for 15 minutes using a three-one motor to prepare an epoxy resin solution (E).

The average layer thickness of the siloxane compound-containing layer was calculated as follows.

The flexible-tube base produced as described above was cut at five positions at random, and each cross section of the siloxane compound-containing layer was observed with a scanning electron microscope (S-5500 (trade name), manufactured by Hitachi High-Tech Corporation) at a magnification of 50,000. Thus, the thickness of the siloxane compound-containing layer formed on the outer periphery was determined at one point in each cross section. The average value calculated from the five determined thickness values was defined as the average layer thickness.

Formation of Primer Layer

A coating liquid for forming a primer layer was prepared by mixing 150 g of ethanol, 350 g of water, and 1.0 g of N-2-(aminoethyl)-3-aminopropylmethyldimethoxysilane (SI-1, trade name: KBM-603, manufactured by Shin-Etsu Chemical Co., Ltd.).

The flexible-tube base having the siloxane compound-containing layer was immersed in the above-prepared coating liquid for forming a primer layer at room temperature for one minute, air-dried for 10 minutes, then placed in an oven at 100° C., and dried by heating for 10 minutes to prepare a flexible-tube base having a primer layer on the siloxane compound-containing layer (flexible-tube base used in Example 1).

In the same manner as described above, flexible-tube bases used in Examples and Comparative Examples were prepared using the raw materials as shown in Table 2 (Tables 2-1 and 2-2). In Comparative Examples 3 and 9, no primer layer was formed.

Formation of Polymer Cover Layer

The outer peripheries of the flexible-tube bases having the primer layer on the siloxane compound-containing layer or the epoxy resin layer were each covered with a polymer as shown in Table 2 below by extrusion (molding temperature: melting point of polymer+10° C.) to produce flexible tubes for endoscopes, the flexible tubes having a polymer cover layer. The polymer cover layer had a thickness of 0.4 mm (in the case of a two-layer structure, the total thickness of the two layers was 0.4 mm).

In the cases where the polymer cover layer was formed of two layers, the outer periphery was simultaneously covered with the two layers by two-layer extrusion molding. In these cases, the proportion of the inner layer to the outer layer at the distal end and the proportion at the proximal end were inner layer:outer layer=80:20 at the distal end and inner layer:outer layer=20:80 at the proximal end, respectively. The thicknesses of the inner layer and the outer layer were changed in a gradient manner from the distal end toward the proximal end.

Each of the produced flexible tubes was subjected to the following tests. The results are summarized in Table 2 below.

[Test Example 1] Evaluation of Elasticity of Flexible Tube

In an environment at a temperature of 25° C. and a relative humidity of 50%, positions 30 cm and 50 cm from one tip portion of the above-produced flexible tube for an endoscope were fixed, and a position of 40 cm (central portion of the flexible tube) was pushed by 15 mm in a direction (diameter direction) perpendicular to the length direction of the flexible tube. A ratio of a repulsive force (b) after 30 seconds to a repulsive force (a) after 0.1 seconds was measured as an elasticity (%). The repulsive force was measured with a force gauge (ZTS50N (trade name), manufactured by IMADA Co., Ltd.).

$$[\text{Elasticity }(\%)]=[(b)/(a)]\times100$$

The elasticity was evaluated on the basis of the evaluation criteria described below. "C" or higher is satisfactory.
Evaluation Criteria for Elasticity
    A: The elasticity is 80% or more.
    B: The elasticity is 75% or more and less than 80%.
    C: The elasticity is 65% or more and less than 75%.
    D: The elasticity is less than 65%.

[Test Example 2] Evaluation of Thermal Durability of Flexible Tube

The above-produced flexible tube for an endoscope was continuously heated at 60° C. for 1,500 hours with a thermo-hygrostat (KHWV-40HP (trade name), manufactured by SATAKE MultiMix Corporation).

The flexible tube for an endoscope before the heating treatment and the flexible tube for an endoscope after the heating treatment were subjected to the following peeling test.
Peeling Test
    A cut with a width of 1 cm was made in the polymer cover layer of the flexible tube for an endoscope in the axial direction of the flexible tube such that the cut reached the flexible-tube base. The formed cut with a width of 1 cm has a width of 1 cm on the outer peripheral surface of the polymer cover layer. A 90° peel strength between the flexible-tube base and the polymer cover layer (the innermost layer in the case of two layers) was measured by gripping an edge of the prepared cut with a width of 1 cm and peeling the polymer cover layer at a constant rate in the axial direction of the flexible tube while maintaining an angle of 90° between the flexible-tube base and the peeled polymer cover layer. The peel strength is a value measured with a force gauge and is expressed in units of N/cm.

A ratio $\{(\text{PSA}(1)/\text{PSB}(1))\times100(\%)\}$ of "PSA(1)" to "PSB(1)" was determined and evaluated on the basis of the evaluation criteria described below, where "PSB(1)" represents the 90° peel strength of the flexible tube for an endoscope before the heating treatment, and "PSA(1)" represents the 90° peel strength of the flexible tube for an endoscope after the heating treatment. "C" or higher is satisfactory.
Evaluation Criteria for Thermal Durability
    AA: 90% or more
    A: 80% or more and less than 90%
    B: 60% or more and less than 80%
    C: 40% or more and less than 60%
    D: less than 40%

[Test Example 3] Evaluation of Hydrogen Peroxide Solution Resistance

Both ends of the above-produced flexible tube for an endoscope were capped with Teflon (registered trademark) plugs, and the flexible tube was immersed in a 5.0% hydrogen peroxide solution at 55° C. for 150 hours. After immersion, the surface was thoroughly washed with water to prepare a flexible tube for an endoscope after immersion in the hydrogen peroxide solution.

The flexible tube for an endoscope before the immersion in the hydrogen peroxide solution and the flexible tube for an endoscope after the immersion in the hydrogen peroxide solution were subjected to the peeling test as in Test Example 2 to measure the peel strengths. A ratio $\{(\text{PSA}(2)/\text{PSB}(2))\times100(\%)\}$ of "PSA(2)" to "PSB(2)" was determined and evaluated on the basis of the evaluation criteria described below, where "PSB(2)" represents the 90° peel strength of the flexible tube for an endoscope before the immersion in the hydrogen peroxide solution, and "PSA(2)" represents the 90° peel strength of the flexible tube for an endoscope after the immersion in the hydrogen peroxide solution. "C" or higher is satisfactory.
Evaluation Criteria for Hydrogen Peroxide Solution Resistance
    AA: 90% or more
    A: 80% or more and less than 90%
    B: 60% or more and less than 80%
    C: 40% or more and less than 60%
    D: less than 40%

TABLE 2-1

|  |  | Ex. 1 | Ex. 2 | Ex. 3 | Ex. 4 | Ex. 5 | Ex. 6 | Ex. 7 | Ex. 8 | Ex. 9 | Ex. 10 |
|---|---|---|---|---|---|---|---|---|---|---|---|
| Siloxane compound-containing layer | Type | (L-1) | (L-2) | (L-3) | (L-4) | (L-5) | (L-6) | (L-7) | (L-8) | (L-9) | (L-10) |
|  | Average layer thickness | 50 nm | 10 nm | 20 nm | 30 nm | 50 nm | 80 nm | 120 nm | 180 nm | 260 nm | 360 nm |
|  | Primer layer | (SI-1) | (SI-1) | (SI-1) | (SI-1) | (SI-1) | (SI-1) | (SI-1) | (SI-1) | (SI-1) | (SI-1) |
| Polymer cover layer | Inner layer | (U-1) | (U-1) | (U-1) | (U-1) | (U-1) | (U-1) | (U-1) | (U-1) | (U-1) | (U-1) |
|  | Outer layer | (E-1) | (E-1) | (E-1) | (E-1) | (E-1) | (E-1) | (E-1) | (E-1) | (E-1) | (E-1) |

TABLE 2-1-continued

| | | | | | | | | | | | |
|---|---|---|---|---|---|---|---|---|---|---|---|
| Elasticity | | A | A | A | A | A | A | A | A | A | A |
| Thermal durability | | A | A | A | AA | AA | AA | A | B | B | C |
| Hydrogen peroxide solution resistance | | AA | C | B | A | AA | AA | AA | A | A | A |

| | | Ex. 11 | Ex. 12 | Ex. 13 | Ex. 14 | Ex. 15 | Ex. 16 | Ex. 17 | Ex. 18 | Ex. 19 | Ex. 20 |
|---|---|---|---|---|---|---|---|---|---|---|---|
| Siloxane compound-containing layer | Type | (L-6) | (L-6) | (L-6) | (L-6) | (L-6) | (L-6) | (L-6) | (L-6) | (L-6) | (L-6) |
| | Average layer thickness | 80 nm | 80 nm | 80 nm | 80 nm | 80 nm | 80 nm | 80 nm | 80 nm | 80 nm | 80 nm |
| Primer layer | | (SI-2) | (SI-3) | (SI-4) | (SI-5) | (SI-6) | (SI-7) | (SI-8) | (SI-9) | (AL-1) | (AL-2) |
| Polymer cover layer | Inner layer | (U-1) | (U-1) | (U-1) | (U-1) | (U-1) | (U-1) | (U-1) | (U-1) | (U-1) | (U-1) |
| | Outer layer | (E-1) | (E-1) | (E-1) | (E-1) | (E-1) | (E-1) | (E-1) | (E-1) | (E-1) | (E-1) |
| Elasticity | | A | A | A | A | A | A | A | A | B | A |
| Thermal durability | | AA | A | A | A | A | A | B | A | C | B |
| Hydrogen peroxide solution resistance | | AA | A | A | A | B | B | A | B | C | B |

| | | Ex. 21 | Ex. 22 | Ex. 23 | Ex. 24 | Ex. 25 | Ex. 26 | Ex. 27 | Ex. 28 | Ex. 29 | Ex. 30 |
|---|---|---|---|---|---|---|---|---|---|---|---|
| Siloxane compound-containing layer | Type | (L-6) | (L-6) | (L-6) | (L-6) | (L-6) | (L-6) | (L-6) | (L-6) | (L-6) | (L-6) |
| | Average layer thickness | 80 nm | 80 nm | 80 nm | 80 nm | 80 nm | 80 nm | 80 nm | 80 nm | 80 nm | 80 nm |
| Primer layer | | (AL-3) | (AL-4) | (AL-5) | (ZR-1) | (ZR-2) | (ZR-3) | (ZR-4) | (ZR-5) | (TI-1) | (TI-2) |
| Polymer cover layer | Inner layer | (U-1) | (U-1) | (U-1) | (U-1) | (U-1) | (U-1) | (U-1) | (U-1) | (U-1) | (U-1) |
| | Outer layer | (E-1) | (E-1) | (E-1) | (E-1) | (E-1) | (E-1) | (E-1) | (E-1) | (E-1) | (E-1) |
| Elasticity | | A | A | B | B | C | B | B | C | B | B |
| Thermal durability | | B | B | B | C | C | B | B | B | C | C |
| Hydrogen peroxide solution resistance | | B | B | C | B | C | B | B | C | B | C |

TABLE 2-2

| | | Ex. 31 | Ex. 32 | Ex. 33 | Ex. 34 | Ex. 35 | Ex. 36 | Ex. 37 | Ex. 38 | Ex. 39 | Ex. 40 |
|---|---|---|---|---|---|---|---|---|---|---|---|
| Siloxane compound-containing layer | Type | (L-6) | (L-6) | (L-6) | (L-6) | (L-6) | (L-6) | (L-6) | (L-6) | (L-6) | (L-6) |
| | Average layer thickness | 80 nm | 80 nm | 80 nm | 80 nm | 80 nm | 80 nm | 80 nm | 80 nm | 80 nm | 80 nm |
| Primer layer | | (TI-3) | (TI-4) | (TI-5) | (SI-1) | (SI-1) | (SI-1) | (SI-1) | (SI-1) | (SI-1) | (SI-1) |
| Polymer cover layer | Inner layer | (U-1) | (U-1) | (U-1) | (U-1) | (U-2) | (U-3) | (U-4) | (E-1) | (A-1) | (P-1) |
| | Outer layer | (E-1) | (E-1) | (E-1) | Single layer | Single layer | Single layer | Single layer | Single layer | Single layer | Single layer |
| Elasticity | | B | A | A | C | C | C | C | A | C | C |
| Thermal durability | | B | B | B | A | A | A | A | A | A | C |
| Hydrogen peroxide solution resistance | | C | B | B | A | A | A | A | C | A | C |

| | | Ex. 41 | Ex. 42 | Ex. 43 | Ex. 44 | Ex. 45 | Ex. 46 | Ex. 47 | Ex. 48 |
|---|---|---|---|---|---|---|---|---|---|
| Siloxane compound-containing layer | Type | (L-6) | (L-6) | (L-6) | (L-6) | (L-6) | (L-6) | (L-6) | (L-6) |
| | Average layer thickness | 80 nm | 80 nm | 80 nm | 80 nm | 80 nm | 80 nm | 80 nm | 80 nm |
| Primer layer | | (SI-1) | (SI-1) | (SI-1) | (SI-1) | (SI-1) | (SI-1) | (SI-1) | (SI-1) |
| Polymer cover layer | Inner layer | (E-1) | (U-2) | (U-3) | (U-4) | (A-1) | (P-1) | (U-1) | (U-1) |
| | Outer layer | (U-1) | (E-1) | (E-1) | (E-1) | (E-1) | (E-1) | (A-1) | (P-1) |
| Elasticity | | A | A | A | A | A | B | B | B |
| Thermal durability | | AA | AA | AA | AA | AA | A | AA | AA |
| Hydrogen peroxide solution resistance | | AA | AA | AA | AA | AA | C | AA | AA |

| | | Com. 1 | Com. 2 | Com. 3 | Com. 4 | Com. 5 | Com. 6 | Com. 7 | Com. 8 | Com. 9 |
|---|---|---|---|---|---|---|---|---|---|---|
| Siloxane compound-containing layer | Type | — | (R-1) | (L-6) | (L-6) | (L-6) | — | — | — | (L-1) |
| | Average layer thickness | | 80 nm | 80 nm | 80 nm | 80 nm | | | | 80 nm |
| Primer layer | | | (SI-1) | (SI-1) | — | (SI-1) | (SI-1) | (AL-1) | (ZR-1) | (TI-1) |

TABLE 2-2-continued

| Polymer cover layer | Inner layer<br>Outer layer | (U-1)<br>(E-1) | (U-1)<br>(E-1) | (U-1)<br>(E-1) | (F-1)<br>Single<br>layer | (F-1)<br>(E-1) | (U-1)<br>(E-1) | (U-1)<br>(E-1) | (U-1)<br>(E-1) | (U-1)<br>(E-1) |
|---|---|---|---|---|---|---|---|---|---|---|
| Elasticity | | A | A | D | D | C | A | B | A | D |
| Thermal durability | | D | D | D | D | D | D | D | D | D |
| Hydrogen peroxide solution resistance | | D | D | D | D | D | D | D | D | D |

Notes in Table 2

Ex.: Example

Com.: Comparative Example

In Comparative Example 2, for easy comparison with Examples, the epoxy resin layer (R-1) is shown in the row of the siloxane compound-containing layer.

The abbreviations shown in the above tables are as follows.

Silane Coupling Agents (SI-11):

N-2-(Aminoethyl)-3-aminopropylmethyldimethoxysilane (trade name: KBM-603, manufactured by Shin-Etsu Chemical Co., Ltd.)

(SI-2):

3-Aminopropyltrimethoxysilane (trade name: KBM-903, manufactured by Shin-Etsu Chemical Co., Ltd.)

(SI-3):

N-Methylaminopropyltrimethoxysilane (SI-4):

3-Ureidopropyltrialkoxysilane (trade name: KBE-585, manufactured by Shin-Etsu Chemical Co., Ltd.)

(SI-5):

N-Phenyl-3-aminopropyltrimethoxysilane (trade name: KBM-573, manufactured by Shin-Etsu Chemical Co., Ltd.)

(SI-6):

3-Trimethoxysilylpropylsuccinic anhydride (trade name: X-12-967C, manufactured by Shin-Etsu Chemical Co., Ltd.)

(SI-7):

(3-Methacryloxypropyl)trimethoxysilane (trade name: KBM-503, manufactured by Shin-Etsu Chemical Co., Ltd.)

(SI-8):

3-Glycidoxypropyltrimethoxysilane (trade name: KBM-403, manufactured by Shin-Etsu Chemical Co., Ltd.)

(SI-9):

3-Mercaptopropyltrimethoxysilane (trade name: KBM-803, manufactured by Shin-Etsu Chemical Co., Ltd.)

Aluminum Coupling Agents (AL-1):

Aluminum sec-butoxide (trade name: ASBD, manufactured by Kawaken Fine Chemicals Co., Ltd.)

(AL-2):

Aluminum trisacetylacetonate (trade name: ORGATIX AL-3100, manufactured by Matsumoto Fine Chemical Co., Ltd.)

(AL-3):

Aluminum bisethylacetoacetate monoacetylacetonate (trade name: ORGATIX AL-3200, manufactured by Matsumoto Fine Chemical Co., Ltd.)

(AL-4):

Aluminum trisethylacetoacetate (trade name: ORGATIX AL-3215, manufactured by Matsumoto Fine Chemical Co., Ltd.)

(AL-5):

Aluminum octadecylacetoacetate diisopropylate (trade name: PLENACT AL-M, manufactured by Ajinomoto Fine-Techno Co., Inc.)

Zirconium Coupling Agents (ZR-1):

Zirconium tetra-n-propoxide (trade name: ORGATIX ZA-45, manufactured by Matsumoto Fine Chemical Co., Ltd.)

(ZR-2):

Zirconium tetra-n-butoxide (trade name: ORGATIX ZA-65, manufactured by Matsumoto Fine Chemical Co., Ltd.)

(ZR-3):

Zirconium tetraacetylacetonate (trade name: ORGATIX ZC-150, manufactured by Matsumoto Fine Chemical Co., Ltd.)

(ZR-4):

Zirconium lactate ammonium salt (trade name: ORGATIX ZC-300, manufactured by Matsumoto Fine Chemical Co., Ltd.)

(ZR-5):

Zirconium tri-n-butoxide stearate (trade name: ORGATIX ZC-320, manufactured by Matsumoto Fine Chemical Co., Ltd.)

Titanium Coupling Agents (TI-1):

Tetra-n-butyl titanate (trade name: ORGATIX TA-21, manufactured by Matsumoto Fine Chemical Co., Ltd.)

(TI-2):

n-Butyl titanate dimer (trade name: ORGATIX TA-23, manufactured by Matsumoto Fine Chemical Co., Ltd.)

(TI-3):

Isopropyl triisostearoyl titanate (trade name: PLENACT TTS, manufactured by Ajinomoto Fine-Techno Co., Inc.)

(TI-4):

Dioctyl bis(ditridecyl)phosphate titanate (trade name: PLENACT 46B, manufactured by Ajinomoto Fine-Techno Co., Inc.)

(TI-5):

Diisopropyl bis(dioctyl pyrophosphate) titanate (trade name: PLENACT 38S, manufactured by Ajinomoto Fine-Techno Co., Inc.)

(U-1):

Polyether polyurethane elastomer (trade name: PANDEX T-8185, manufactured by DIC Corporation)

(U-2):

Polyether polyurethane elastomer (trade name: Miractran E380, manufactured by Nippon Polyurethane Industry Co., Ltd.)

(U-3):

Polyester polyurethane elastomer (trade name: Miractran E480, manufactured by Nippon Polyurethane Industry Co., Ltd.)

(U-4):

Polycarbonate polyurethane elastomer (trade name: PANDEX T-9280, manufactured by DIC Corporation)

(E-1):

Polyester elastomer (trade name: PELPRENE P-40B, manufactured by Toyobo Co., Ltd.)

(A-1):

Polyamide elastomer (trade name: Pebax 4533, manufactured by Arkema Inc.)

(P-1):

Polyolefin elastomer: Zelas MC707 (trade name), manufactured by Mitsubishi Chemical Corporation (F-1):

Fluorine-containing elastomer: DAI-EL T-530 (trade name), manufactured by Daikin Industries, Ltd.

Table 2 shows the following.

The flexible tubes of Comparative Examples 1 and 6 to 8, which do not have the siloxane compound-containing layer defined in the present invention, are inferior in thermal durability and hydrogen peroxide solution resistance even though they have the primer layer.

The flexible tube of Comparative Example 2 has an epoxy resin layer instead of the siloxane compound-containing layer between the flexible-tube base and the primer layer. However, this flexible tube is inferior in thermal durability and hydrogen peroxide solution resistance.

The flexible tubes of Comparative Examples 3 and 9 have the siloxane compound-containing layer defined in the present invention but do not have the primer layer defined in the present invention. These flexible tubes are inferior in all of elasticity, thermal durability, and hydrogen peroxide solution resistance.

The flexible tube of Comparative Example 4 has a fluorine-containing elastomer layer serving as a polymer cover layer. The flexible tube of Comparative Example 5 has a fluorine-containing elastomer layer serving as a polymer cover layer on the side in contact with the primer layer. That is, these flexible tubes do not have the polymer cover layer defined in the present invention on the side in contact with the primer layer. The flexible tube of Comparative Example 4 is inferior in all of elasticity, thermal durability, and hydrogen peroxide solution resistance, and the flexible tube of Comparative Example 5 is inferior in thermal durability and hydrogen peroxide solution resistance.

In contrast, the flexible tubes of Examples 1 to 48 according to the present invention have sufficient elasticity and good thermal durability and further have good hydrogen peroxide solution resistance.

REFERENCE SIGNS LIST 2 electronic endoscope (endoscope)
3 insertion section
3a flexible tube
3b angle portion
3c tip portion
5 main-body operation section
6 universal cord
11 spiral tube
11a metal strip
12 tubular mesh member
13 cap
14 flexible-tube base
14a distal end side
14b proximal end side
15 polymer cover layer
16 topcoat layer
17 inner layer
18 outer layer
X angle portion 3b side (soft)

Y main-body operation section 5 side (hard)
20 continuous molding machine (production apparatus)
21, 22 extrusion unit
21a screw
22a screw
23 head unit
24 cooling unit
25 transport unit
26 control unit
28 feed drum
29 take-up drum
30 joint member
31 connected flexible-tube base
32 nipple
33 die
34 support
35, 36 gate
37 molding passage
38 polymer passage
39 first polymer material (soft polymer)
40 second polymer material (hard polymer)

What is claimed is:

1. A flexible tube for an endoscope, the flexible tube comprising:

a flexible-tube base containing metal as a constituent material;

a layer containing a siloxane compound and disposed on the flexible-tube base;

a primer layer on the layer containing the siloxane compound; and a polymer cover layer on the primer layer, wherein the siloxane compound has a hydroxy group, the layer containing the siloxane compound is porous, and the polymer cover layer includes at least one compound of a polyamide, a polyester, a polyurethane, or a polyolefin on a side in contact with the primer layer.

2. The flexible tube for the endoscope according to claim 1, wherein the siloxane compound includes an organosiloxane compound.

3. The flexible tube for the endoscope according to claim 1, wherein the primer layer includes at least one of a silane coupling agent, a titanium coupling agent, a zirconium coupling agent, or an aluminum coupling agent.

4. The flexible tube for the endoscope according to claim 1, wherein the primer layer includes a silane coupling agent.

5. The flexible tube for the endoscope according to claim 1, wherein the primer layer includes an amino silane coupling agent.

6. The flexible tube for the endoscope according to claim 1, wherein the metal that constitutes the flexible-tube base is stainless steel.

7. The flexible tube for the endoscope according to claim 1, wherein the metal that constitutes the flexible-tube base has a passivation film on a surface of the metal.

8. The flexible tube for the endoscope according to claim 1, wherein the polymer cover layer has a single-layer structure or a multilayer structure and includes at least one compound of a polyamide, a polyester, a polyurethane, or a polyolefin in a layer in contact with the primer layer.

9. The flexible tube for the endoscope according to claim 1, wherein the polymer cover layer has a two-layer structure, and a proportion of a thickness of an inner layer to a thickness of an outer layer of the two-layer structure changes in a gradient manner in an axial direction of the flexible-tube base.

10. The flexible tube for the endoscope according to claim 9, wherein the proportion of the thickness of the inner layer to the thickness of the outer layer is inner layer:outer layer=95:5 to 60:40 at one end of the flexible tube for the endoscope and is inner layer:outer layer=5:95 to 40:60 at the other end.

11. An endoscopic medical device comprising the flexible tube for the endoscope according to claim 1.

12. A method for producing a flexible tube for an endoscope, the method comprising:

forming, on a flexible-tube base containing metal as a constituent material, a layer containing a siloxane compound;

forming a primer layer on the layer containing the siloxane compound; and forming a polymer cover layer on the primer layer, wherein the siloxane compound has a hydroxy group, the layer containing the siloxane compound is porous, and the polymer cover layer includes at least one compound of a polyamide, a polyester, a polyurethane, or a polyolefin on a side in contact with the primer layer.

13. A method for producing an endoscopic medical device, the method comprising incorporating, into an insertion section of the endoscopic medical device, the flexible tube for the endoscope obtained by the method for producing the flexible tube for the endoscope according to claim 12.

14. A method for producing an endoscopic medical device, the method comprising incorporating, into an insertion section of the endoscopic medical device, the flexible tube for the endoscope according to claim 1.

* * * * *